United States Patent
Crosby et al.

(10) Patent No.: US 11,993,792 B2
(45) Date of Patent: May 28, 2024

(54) DNASE I VARIANTS, COMPOSITIONS, METHODS, AND KITS

(71) Applicant: New England Biolabs, Inc., Ipswich, MA (US)

(72) Inventors: Heidi Crosby, Ipswich, MA (US); Jennifer Ong, Salem, MA (US); Ashley Luck, Ipswich, MA (US); Eric J. Cantor, Topsfield, MA (US); Vladimir Potapov, Auburndale, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 17/332,821

(22) Filed: May 27, 2021

(65) Prior Publication Data

US 2022/0380741 A1 Dec. 1, 2022

(51) Int. Cl.
*C12N 9/22* (2006.01)
*C07K 14/47* (2006.01)

(52) U.S. Cl.
CPC ............ *C12N 9/22* (2013.01); *C07K 14/4702* (2013.01); *C07K 2319/02* (2013.01); *C07K 2319/20* (2013.01)

(58) Field of Classification Search
CPC .. C12N 9/22; C07K 14/4702; C07K 2319/02; C07K 2319/20; C07K 2319/10
See application file for complete search history.

(56) References Cited

U.S. PATENT DOCUMENTS

| | | |
|---|---|---|
| 6,348,343 B2 | 2/2002 | Lazarus et al. |
| 6,391,607 B1 | 5/2002 | Lazarus et al. |
| 6,627,424 B1 | 9/2003 | Wang |
| 7,067,298 B2 | 6/2006 | Latham et al. |
| 7,297,526 B2 | 11/2007 | Shak |
| 7,803,922 B2 | 9/2010 | Lukyanov et al. |
| 7,888,090 B2 | 2/2011 | Barnikow et al. |
| 7,939,284 B2 | 5/2011 | Johnsson et al. |
| 7,951,569 B2 | 5/2011 | Hirakawa et al. |
| 8,535,925 B2 | 9/2013 | Ramaswamy et al. |
| 8,551,753 B2 | 10/2013 | Lanes et al. |
| 9,133,447 B2 | 9/2015 | Lanes et al. |
| 10,041,051 B2 | 8/2018 | Hsieh et al. |
| 10,876,149 B2 | 12/2020 | Becker |
| 11,312,968 B2 | 4/2022 | Dai et al. |
| 2004/0248272 A1 | 12/2004 | Muller et al. |
| 2011/0020878 A1 | 1/2011 | Lanes et al. |
| 2016/0026574 A1 | 1/2016 | Frank et al. |
| 2018/0187242 A1 | 7/2018 | Makrigiorgos et al. |
| 2019/0127783 A1 | 5/2019 | Becker |
| 2021/0285032 A1 | 9/2021 | Becker |
| 2021/0308031 A1 | 10/2021 | Dai et al. |
| 2021/0355173 A1 | 11/2021 | Vogl et al. |
| 2022/0162592 A1 | 5/2022 | Lin et al. |

FOREIGN PATENT DOCUMENTS

| | | |
|---|---|---|
| EP | 1431387 B1 | 2/2008 |
| WO | 2004/090114 A2 | 10/2004 |
| WO | 2010117901 A1 | 10/2010 |
| WO | 2016026574 A1 | 2/2016 |
| WO | 2020/106709 A1 | 5/2020 |

OTHER PUBLICATIONS

Scally, A., UniProtKB accession No. G3QY47, Nov. 16, 2011.*
UniProtKB accession No. A0A2Y9F0H5, Sep. 12, 2018.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
Zacchia et al., Kidney Disease 2(2):72-79, 2016.*
Genbank accession No. XP_005697533, Sep. 8, 2016.*
GenBank accession No. XP_010838694, Dec. 31, 2014.*
Altschul, et al., J. Mol. Biol., 215, 403-410, 1990.
Tolun, et al., Nucleic Acids Resarch, 31, 18, e111, 2003.
Pan, et al. Ca2+-dependent activity of human DNase I and its hyperactive variants, Protein Science (1999), 8(9), 1780-1788.
Pan, et al. Hyperactivity of human DNase I variants. Dependence on the No. of positively charged residues and concentration, length, and environment of DNA, Journal of Biological Chemistry (1998), 273(19), 11701-11708.
Pan, et al., Improved potency of hyperactive and actin-resistant human DNase I variants for treatment of cystic fibrosis and systemic lupus erythematosus, Journal of Biological Chemistry (1998), 273(29), 18374-18381.
Pan, et al., Engineering Hyperactive Variants of Human Deoxyribonuclease I by Altering Its Functional Mechanism, Biochemistry, 1997, 36, 6624-6632.
Lahm, et al., DNAse I-induced DNA Conformation 2 A Structure of a DNase I-Octamer Complex, J. Mol. Biol., 1991, 221, 645-667.
Weston, et al., X-ray Structure of the DNase I-d(GGTATACC)2 Complex at 2-3 A Resolution, J. Mol. Biol, 1992, 226, 1237-1256.
Evans, et al., Site-Directed Mutagenesis of Phosphate-Contacting Amino Acid of Bovine Pancreatic Deoxyribonuclease I, Biochemistry, 1999, 38, 3902-3909.
Wu, et al., Recent advances in duplex-specific nuclease-based signal amplification strategies for microRNA detection, Biosensors and Bioelectronics, 165, 112449, 2020.

(Continued)

*Primary Examiner* — Delia M Ramirez
(74) *Attorney, Agent, or Firm* — New England Biolabs, Inc

(57) ABSTRACT

The present disclosure relates, according to some embodiments, to systems, apparatus, compositions, methods, and workflows that include DNase I variants with desirable properties including, for example, salt tolerance. A DNase I variant, in some embodiments, may have an amino acid sequence that is at least 85% identical, at least 90% identical, at least 95% identical, and/or at least 98% identical to SEQ ID NO:1 and may be identical to SEQ ID NO:1 at one or more positions selected from the group of positions corresponding to L29, A35, D87, Q88, S94, P103, T108, P121, P132, A135, D145, E161, G172, P190, H208, and A224 of SEQ ID NO:1.

24 Claims, 12 Drawing Sheets

Specification includes a Sequence Listing.

(56) References Cited

OTHER PUBLICATIONS

Archer, et al., Selective and flexible depletion of problematic sequences from RNA-seq libraries at the cDNA stage, BMC Genomics, 15:401, 2014.
Yi, et al., Duplex-specific nuclease efficiently removes rRNA for prokaryotic RNA-seq, Nucleic Acids Rsearch, 39, 20, e140, 2011.
Xiao, et al., High-throughput RNA sequencing of a formalin-fixed, paraggin-embedded autopsy lung tissue sample from the 1918 influenza pandemic, J Pathol., 229:4, 535-545, 2013.
Zhulidov, et al., Simple cDNA normalization using kamchatka crab duplex-specific nuclease, Nucleic Acids Rsearch, 32, 3, e37, 2004.

\* cited by examiner

```
SEQ ID NO:1 Variant7   LKIAAFNIRTFGETKMSNATLASYIVRILR   30
SEQ ID NO:2 human      LKIAAFNIQTFGETKMSNATLVSYIVQILS   30
SEQ ID NO:3 bovine     LKIAAFNIRTFGETKMSNATLASYIVRIVR   30
                       *******:*************.****:*:

SEQ ID NO:1 Variant7   RYDIALIQEVRDSHLVAVGKLLDYLNQDDP   60
SEQ ID NO:2 human      RYDIALVQEVRDSHLTAVGKLLDNLNQDAP   60
SEQ ID NO:3 bovine     RYDIVLIQEVRDSHLVAVGKLLDYLNQDDP   60
                       ****.*:********.*******.**** *

SEQ ID NO:1 Variant7   NTYHYVVSEPLGRNSYKERYLFLFRPDQVS   90
SEQ ID NO:2 human      DTYHYVVSEPLGRNSYKERYLFVYRPDQVS   90
SEQ ID NO:3 bovine     NTYHYVVSEPLGRNSYKERYLFLFRPNKVS   90
                       :*********************::**::**

SEQ ID NO:1 Variant7   VLDSYQYDDGCEPCGNDTFSREPAVVKFSS   120
SEQ ID NO:2 human      AVDSYYYDDGCEPCGNDTFNREPAIVRFFS   120
SEQ ID NO:3 bovine     VLDTYQYDDGCESCGNDSFSREPAVVKFSS   120
                       .:*:* ****** ****:*.****:*:*:*

SEQ ID NO:1 Variant7   PSTKVKEFAIVPLHAAPSDAVAEIDSLYDV   150
SEQ ID NO:2 human      RFTEVREFAIVPLHAAPGDAVAEIDALYDV   150
SEQ ID NO:3 bovine     HSTKVKEFAIVALHSAPSDAVAEINSLYDV   150
                        *::****** **:**.*******:.****

SEQ ID NO:1 Variant7   YLDVQQKWHLEDVMLMGDFNAGCSYVTSSQ   180
SEQ ID NO:2 human      YLDVQEKWGLEDVMLMGDFNAGCSYVRPSQ   180
SEQ ID NO:3 bovine     YLDVQQKWHLNDVMLMGDFNADCSYVTSSQ   180
                       *****:** *:*********.****  **

SEQ ID NO:1 Variant7   WSSIRLRTSPTFQWLIPDSADTTATSTHCA   210
SEQ ID NO:2 human      WSSIRLWTSPTFQWLIPDSADTTATPTHCA   210
SEQ ID NO:3 bovine     WSSIRLRTSSTFQWLIPDSADTTATSTNCA   210
                       ****** ** ***************.:**

SEQ ID NO:1 Variant7   YDRIVVAGSLLQSAVVPGSAAPFDFQAAYG   240
SEQ ID NO:2 human      YDRIVVAGMLLRGAVVPDSALPFNFQAAYG   240
SEQ ID NO:3 bovine     YDRIVVAGSLLQSSVVPGSAAPFDFQAAYG   240
                       ********:**:.:***.**:**:******

SEQ ID NO:1 Variant7   LSNEMALAISDHYPVEVTLT 260
SEQ ID NO:2 human      LSDQLAQAISDHYPVEVMLK 260
SEQ ID NO:3 bovine     LSNEMALAISDHYPVEVTLT 260
                       **::::* ********* *.
```

FIG. 2

DNASE I VARIANTS, COMPOSITIONS, METHODS, AND KITS

SEQUENCE LISTING STATEMENT

This disclosure includes a Sequence Listing submitted electronically in ascii format under the file name "NEB-437_ST25.txt". This Sequence Listing is incorporated herein in its entirety by this reference.

BACKGROUND

The chemical stability of DNA supports its role as a molecular repository of genetic information. This stability can be undesirable in certain contexts where, for example, its persistence can contribute to the genesis and/or pathology of cancer and other diseases. Its presence can also impair sample analysis, for example, when studying RNA. DNA's stability is limited, and it is subject to damage and many chemical and biological agents exist which can digest it. One such agent is DNase I, which is an endonuclease that creates single strand nicks in double stranded DNA under physiological conditions. Accumulation of such nicks may ultimately result in fragmentation of the double-stranded molecule. The activity of DNase I may be limited or blocked under some conditions. For example, the activity of DNase I may be compromised in the absence of salt, in the absence of $Ca^{2+}$, in the absence of $Mg^{2+}$, or in the presence of high salt (e.g., above 250 mM), which may limit its utility in analytical workflows.

SUMMARY

The present disclosure provides systems, apparatus, compositions, methods, and workflows that include DNase I variants with desirable properties including, for example, salt tolerance. A DNase I variant, in some embodiments, may have an amino acid sequence that is at least 85% identical, at least 90% identical, at least 95% identical, and/or at least 98% identical to SEQ ID NO:1 and may be identical to SEQ ID NO:1 at one or more positions selected from the group of positions corresponding to L29, A35, D87, Q88, S94, P103, T108, P121, P132, A135, D145, E161, G172, P190, H208, and A224 of SEQ ID NO:1. For example, a DNase I variant may have (or may further have) an amino acid sequence identical to SEQ ID NO:1 at one or more positions selected from the group of positions corresponding to E13, N18, S43, H44, N74, S75, P103, N106, T205, S206, and T207 of SEQ ID NO:1. For example, a DNase I variant may have (or may further have) an amino acid sequence identical to SEQ ID NO:1 at one or more positions selected from the group of positions corresponding to S22, S30, T46, and I163 of SEQ ID NO:1. A DNase I variant may have an amino acid sequence comprising one, two, three or more substitutions at positions corresponding to SEQ ID NO:1, the substitutions and corresponding positions selected from E13K, E13R, N18A, A35V, S43K, S43R, H44K, H44R, N74K, N74R, S75K, S75R, P103S, N106A, T205K, T205R, S206K, S206R, T207K, and T207R.

According to some embodiments, a DNase I variant may have an amino acid sequence at least 85% identical, at least 88% identical, at least 90% identical, at least 92% identical, at least 95% identical, at least 98% identical, and/or at least 99% identical to SEQ ID NO:1 and comprise one, two or more of: (a) a lysine or arginine at a position corresponding to position 13 of SEQ ID NO:1, (b) a lysine or arginine at a position corresponding to position 43 of SEQ ID NO:1, (c) a lysine or arginine at a position corresponding to position 44 of SEQ ID NO:1, (d) a lysine or arginine at a position corresponding to position 74 of SEQ ID NO:1, (e) a lysine or arginine at a position corresponding to position 75 of SEQ ID NO:1, (f) a lysine or arginine at a position corresponding to position 205 of SEQ ID NO:1, (g) a lysine or arginine at a position corresponding to position 206 of SEQ ID NO:1, and (h) a lysine or arginine at a position corresponding to position 207 of SEQ ID NO:1. A DNase I variant may have (or may further have) an amino acid sequence comprising one or more of (a) a valine at a position corresponding to position 35 of SEQ ID NO:1, and (b) a serine at a position corresponding to position 103 of SEQ ID NO:1. An amino acid sequence of a DNase I variant may have one or more positions that are not identical to their corresponding position of SEQ ID NO: 1 including, for example, one or more positions corresponding to E13, N18, A35, S43, H44, N74, S75, P103, N106, T205, S206, and T207 of SEQ ID NO:1.

In some embodiments, a DNase I variant may comprise an amino acid sequence at least 85% identical, at least 88% identical, at least 90% identical, at least 92% identical, at least 95% identical, at least 98% identical, at least 99% identical, and/or identical to the amino acid sequence of SEQ ID NO: 1, 5, 7, 8, or 9.

In some embodiments, a DNase I variant may comprise an amino acid sequence at least 85% identical, at least 88% identical, at least 90% identical, at least 92% identical, at least 95% identical, at least 98% identical, at least 99% identical, and/or identical to the amino acid sequence of SEQ ID NO: 6 or 11. For example, a DNase I variant may have an amino acid sequence, wherein (a) X13 is any amino acid other than E, (b) X18 is any amino acid other than N, (c) X35 is any amino acid other than V, (d) X43 is any amino acid other than S, (e) X44 is any amino acid other than H, (f) X74 is any amino acid other than N, (g) X75 is any amino acid other than S, (h) X103 is any amino acid other than S, (i) X106 is any amino acid other than N, (j) X135 is any amino acid other than S, (k) X205 is any amino acid other than T, (l) X206 is any amino acid other than P and S, (m) X207 is any amino acid other than T, or (n) any combination of two or more of (a)-(m). A DNase I variant may have an amino acid sequence, for example, wherein (a) X13 is K or R, (b) X18 is A, (c) X35 is V, (d) X43 is K or R, (e) X44 is K or R, (f) X74 is K or R, (g) X75 is K or R, (h) X103 is P or S, (i) X106 is A, (j) X135 is A, (k) X205 is K, R or T, (l) X206 is K, P, R or S, (m) X207 is K, R or T, or (n) any combination of two or more of (a)-(l).

The present disclosure relates to salt tolerant DNase I variants. For example, a DNase I variant may have at least 30% of its peak catalytic activity over a range of total salt concentrations of 0 mM to 300 mM. Peak activity in this context is the highest observed catalytic activity in reactions representing the full range of total salt concentrations, but otherwise maintained under the same conditions (e.g., buffer, temperature, reaction time, type and quantity of substrate, quantity of enzyme). For example, to assess peak catalytic activity empirically, a DNase I variant may be divided into a plurality of aliquots. Each aliquot may be combined with a buffering agent, a test substrate (e.g., FIG. 1), and differing concentrations of salt (e.g., 0 mM, 100 mM, 200 mM, and 300 mM), incubated for a selected time at a selected temperature, and assayed for DNase activity by any method provided herein or otherwise available. Peak activity for the DNase I variant assayed would be the highest observed activity among the tested concentrations (e.g., 0 mM, 100 mM, 200 mM, and 300 mM). The activity at the other salt concentrations may be expressed as a percentage of the peak activity.

In some embodiments, a DNase I variant may have an amino acid sequence comprising one or more substitutions at positions corresponding to SEQ ID NO:3, the substitutions and corresponding positions selected from N18A, V35X, S43K, S43R, S103X, N106A, S206K, S206R, T207K, and T207R.

The present disclosure relates to non-naturally occurring fusion proteins having a single polypeptide chain comprising any DNase I variant disclosed herein and any other peptide or polypeptide. For example, a fusion protein may comprise a single polypeptide chain, the single peptide chain comprising (a) a DNase I variant, and at least one of an affinity tag, a secretion signal, and a linker. Each of an affinity tag, a secretion signal, and a linker may be linked to the amino-terminal end, the carboxy-terminal end or an amino acid side chain along the length of a DNase I variant.

The present disclosure also relates to methods for treating a composition (e.g., a bodily or other fluid or specimen, a cell, a cell extract, a clinical sample or specimen), wherein the composition comprises or may comprise DNA and/or RNA. For example, a method may comprise contacting a composition with any DNase I variant disclosed herein to form a reaction mixture. A reaction mixture may lack salt (e.g., free of salt) or may comprise a total salt concentration of at least 50 mM, at least 100 mM, at least 200 mM, or at least 300 mM. A method, in some embodiments, may comprise one or more products of DNA hydrolysis. A method for hydrolyzing DNA may comprise contacting (a) a composition comprising DNA and optionally RNA, and (b) a DNase according to any of the preceding Claims (e.g., under conditions including time, temperature, pH, buffer, salt) to form a reaction mixture comprising DNA hydrolysis products (e.g., wherein at least a portion of the DNA hydrolysis products arise from hydrolysis of the DNA in the composition). A reaction mixture may have a total salt concentration of 0 mM to 300 mM. In some embodiments, a DNase I variant may hydrolyze DNA efficiently (with or without salt present) without substantial impact on the RNA present. For example, a composition may comprise RNA and the reaction mixture may comprise at least 90% of the RNA that was in the composition (e.g., after >2, >5, >10, >15, >10, >15, >30 minutes from initial contacting). A reaction mixture may comprise less than 10% of the DNA that was in the composition (e.g., after >2, >5, >10, >15, >10, >15, >30 minutes from initial contacting). In some embodiments, a reaction mixture may comprise a DNase I buffer or a high magnesium buffer.

The present disclosure provided, in some embodiments, compositions comprising a DNase I variant. For example, a composition may comprise any of the disclosed DNase I variants and one or more salts at a total salt concentration of at least 50 mM. A composition may further comprise one or more enzymes other than the DNase I variant (e.g., an RNA polymerase).

BRIEF DESCRIPTION OF THE FIGURES

FIG. 2 shows a sequence alignment of DNase variant V7 (SEQ ID NO:1), human DNase I (SEQ ID NO:2), and bovine DNase I (SEQ ID NO:3).

FIG. 4A shows DNase activity measured in DNase I buffer. FIG. 4B shows DNase activity measured in DNase I buffer supplemented with 200 mM NaCl. FIG. 4C shows DNase activity measured in high-$Mg^{2+}$- buffer (4C).

DETAILED DESCRIPTION

Figure 1:
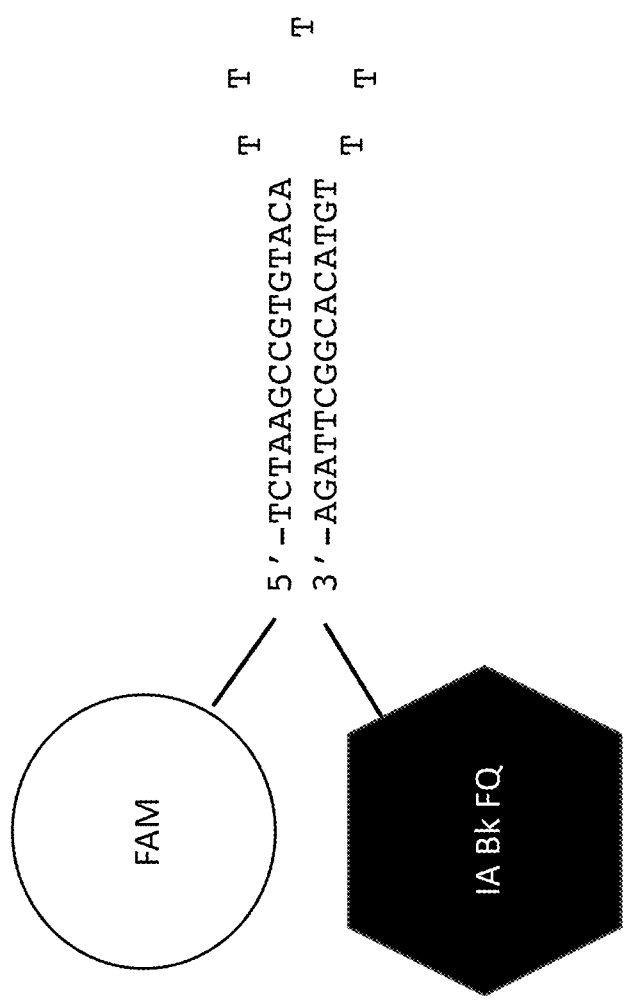
FIG. 1 shows a fluorescent probe comprising a 35 nt DNA oligo (SEQ ID NO: 12) with a 5' FAM label and a 3' quencher (Iowa Black FQ). When the probe is heated to 95° C. and then gradually cooled, it folds into a hairpin structure in which the quencher quenches the fluorophore. Cleavage of the DNA hairpin by DNase I releases FAM, resulting in an increase in fluorescence that can be measured at 517 nm using a spectrophotometer. For screening of mutants, typical reactions contained 3 µM probe in a 30 µl reaction, and reactions were carried out in black half-area 96-well plates (costar 3694).

The present disclosure provides DNase I variants, fusions, compositions, methods, and workflows for cleaving DNA. DNase I variants, according to some embodiments, may have catalytic activity in the presence of higher salt concentrations than wild type DNase I.

GENERAL CONSIDERATIONS

Aspects of the present disclosure can be further understood in light of the embodiments, section headings, figures, descriptions and examples, none of which should be construed as limiting the entire scope of the present disclosure in any way. Accordingly, the claims set forth below should be construed in view of the full breadth and spirit of the disclosure.

Each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Unless otherwise defined, all technical and scientific terms used herein have the same meaning as commonly understood by one of ordinary skill in the art to which this disclosure belongs. Still, certain terms are defined herein with respect to embodiments of the disclosure and for the sake of clarity and ease of reference.

Sources of commonly understood terms and symbols may include: standard treatises and texts such as Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); Singleton, et al., Dictionary of Microbiology and Molecular biology, 2d ed., John Wiley and Sons, New York (1994), and Hale & Markham, the Harper Collins Dictionary of Biology, Harper Perennial, N.Y. (1991) and the like.

As used herein and in the appended claims, the singular forms "a" and "an" include plural referents unless the context clearly dictates otherwise. For example, the term "a protein" refers to one or more proteins, i.e., a single protein and multiple proteins. It is further noted that the claims can be drafted to exclude any optional element. As such, this statement is intended to serve as antecedent basis for use of such exclusive terminology as "solely," "only" and the like in connection with the recitation of claim elements or use of a "negative" limitation.

Numeric ranges are inclusive of the numbers defining the range. All numbers should be understood to encompass the midpoint of the integer above and below the integer i.e., the number 2 encompasses 1.5-2.5. The number 2.5 encompasses 2.45-2.55 etc. When sample or example numerical values are provided, each alone may represent an intermediate value in a range of values and/or each may be combined with other sample or example values as the extremes of a range unless specified. For example, disclosures of values 42 and 53 in a figure and a value of 64 (with the same units) in a table may be intermediates in one or more ranges (e.g., 40-70, 35-75, and 30-80) and/or may be combined as endpoints of ranges 42-53, 42-64, and 53-64.

As used herein, "buffering agent", refers to an agent that allows a solution to resist changes in pH when acid or alkali is added to the solution. Examples of suitable non-naturally occurring buffering agents that may be used in the compositions, kits, and methods of the invention include, for example, Tris, HEPES, TAPS, MOPS, tricine, or MES. A buffer composition may comprise a buffering agent and one or more additional components including, for example, salts (e.g., NaCl, $MgCl_2$), surfactants, detergents, stabilizers, and combinations thereof. Buffer compositions may be concentrated (e.g., 10×), dried, or lyophilized and subsequently diluted or wetted to a desired final working concentration. Buffer compositions include commercially available compositions (e.g., DNase I Reaction Buffer and/or high magnesium buffer).

As used herein, "catalytically active" refers to the property of a molecule (e.g., a proteinaceous molecule or macromolecule) to function as a catalyst of one or more chemical reactions relative to one or more substrates and products. A catalytically active DNase I or DNase I variant, for example, hydrolyzes one or more polydeoxyribonuceic acids to yield (however briefly) products comprising at least one 5'-phosphorylated oligonucleotide. Catalytic activity of DNase I and/or DNase I variants may be assessed using existing techniques applied to one or more model substrates and/or one or more substrates of interest. For example, effective assays for catalytic activity of DNase I may include size fractionation of products (e.g., on gels or other matrices), radioactive assays, and fluorometric assays (e.g., #234056, #abab252898, AbCam PLC, Cambridge, U.K.; PicoGreen, Nucl. Acids Res. 2003 31(18):e111)). Catalytic activity may be assessed with respect to loss of original DNA (e.g., percent of original DNA remaining), concentration of DNA (e.g., above 10 nts, above 8 nts, above 6 nts, above, above 3 nts in length, 4 nts, or above 2 nts in length), and/or metrics that serve as a proxy thereof.

With respect to polydeoxyribonucleic acid, "digest," as used herein, refers to hydrolyzing or otherwise reducing the size of such polydeoxyribonucleic acid. Unless qualified, digesting a polydeoxyribonucleic acid includes all degrees of hydrolyzing or otherwise reducing the size of such polydeoxyribonucleic acid, partially up to and including fully. Sites of hydrolysis may be regarded as independent of the nucleotide sequence ("non-specific"), even if some sequence bias is observed under some conditions.

As used herein, "DNase I" refers to any naturally occurring enzyme that hydrolyzes one or more polydeoxyribonucleic acid substrates to yield products comprising at least one 5'-phosphorylated polydeoxyribonucleotide and/or at least one 3'-hydroxylated polydeoxyribonucleotide. A DNase I may display catalytic activity as a phosphodiesterase.

As used herein, "DNase I variant" refers to any non-naturally occurring enzyme that hydrolyzes one or more polydeoxyribonucleic acid substrates to yield products comprising at least one 5'-phosphorylated polydeoxyribonucleotide and/or at least one 3'-hydroxylated polydeoxyribonucleotide.

A DNase I variant may comprise an amino acid sequence having at least 80%, at least 85%, at least 88% identical, at least 90%, at least 92%, at least 93%, at least 95%, at least 96%, at least 97%, at least 98% or at least 99% identity to SEQ ID NO: 1, 5, 6, 7, 8, 9, 10, and/or 11. According to some embodiments, a DNase I variant may comprise an amino acid sequence that (a) is identical to SEQ ID NO:1 at one or more positions corresponding to L29, A35, D87, Q88, S94, P103, T108, P121, P132, A135, D145, E161, G172, P190, H208, and A224 of SEQ ID NO:1, (b) is identical to SEQ ID NO:1 at one or more positions corresponding to E13, N18, S43, H44, N74, S75, P103, N106, T205, S206, and T207 of SEQ ID NO:1, and/or (c) comprises one or more substitutions selected from E13K, E13R, N18A, A22S, R305, A35V, S43K, S43R, H44K, H44R, V46T, N74K, N74R, S75K, S75R, P103S, N106A, V163I, T205K, T205R, S206K, S206R, T207K, and T207R, wherein the reference sequence for such substitutions is SEQ ID NO:1. In some embodiments, a DNase I variant may comprise (a) an amino acid sequence having at least 80%, at least 85%, at least 90%, at least 93%, at least 96%, at least 97%, at least 98% or at least 99% identity to SEQ ID NO: 3, and one or more substitutions selected from N18A, V35X, S43K, S43R, S103X, N106A, S206K, S206R, T207K, and T207R, wherein the reference sequence for such substitutions is SEQ ID NO:3.

A DNase I variant may be salt tolerant and/or salt indifferent. Catalytic activity of a DNase I variant may persist across a range of salt concentrations, temperatures and/or pH. For example, a DNase I variant may display catalytic activity under such a range of conditions and/or following removal from exposure to conditions within such a range. A DNase I variant may have catalytic activity at and/or following exposure to temperatures from 1° C. to 99° C., 10° C. to 90° C., 20° C. to 80° C., 4° C. to 37° C., 5° C. to 95° C., 10° C. to 30° C., 10° C. to 40° C., 10° C. to 50° C., 15° C. to 60° C., 15° C. to 45° C., 15° C. to 75° C., 50° C. to 99° C., 60° C. to 99° C., and/or 70° C. to 99° C. A DNase I variant may have catalytic activity at and/or following exposure to a pH below 4, from 2 to 5, from 2 to 12, from 3 to 5, from 3 to 7, from 3 to 9, from 3 to 11, from 4 to 8, from 4 to 10, from 4 to 12, from 5 to 7, from 5 to 9, from 5 to 12, from 6 to 8, from 6 to 10, from 6 to 12, from 7 to 9, from 7 to 10, from 7 to 11, from 7 to 12, from 9 to 12, from 9 to 13, and/or over 11.

DNase I variants include fusion proteins comprising (a) a first polypeptide having at least 80%, at least 85%, at least 90%, at least 93%, at least 96%, at least 97%, at least 98% or at least 99% identity to SEQ ID NO: 1, 5, 6, 7, 8, 9, 10, and/or 11 and a second polypeptide (e.g., albumin, a DNA-binding domain, or a topoisomerase). DNase I variants include fusions comprising (a) a first polypeptide having at least 80%, at least 85%, at least 90%, at least 93%, at least 96%, at least 97%, at least 98% or at least 99% identity to SEQ ID NO: 1, 5, 6, 7, 8, 9, 10, and/or 11 and (b) one or more additional materials, examples of which include, without limitation, a carbohydrate (e.g., a glycoside), a fatty acid, a surface (e.g., a bead, a plate, or a well), a purification tag (e.g., a histidine tag), a label, and other molecules (e.g., polyethylene glycol). Fusions may be covalently attached at the N-terminal end of the polypeptide, the C-terminal end of the polypeptide, or at an amino acid position (e.g., an amino acid side chain) along the length of the polypeptide. A DNase I variant may comprise one or more modified amino acids (e.g., γ-carboxyglutamic acid, 4-hydroxyproline, 5-hydroxylysine, and selenocysteine) and/or D-amino acids.

As used herein, "fusion protein" refers to a protein composed of two or more polypeptide components that are un-joined in their native state. Fusion proteins may be a combination of two, three or four or more different proteins. For example, a fusion protein may comprise two naturally occurring polypeptides that are not joined in their respective native states. A fusion protein may comprise two polypeptides, one of which is naturally occurring and the other of which is non-naturally occurring. The term polypeptide is not intended to be limited to a fusion of two heterologous amino acid sequences. A fusion protein may have one or more heterologous domains added to the N-terminus, C-terminus, and or the middle portion of the protein. If two parts of a fusion protein are "heterologous", they are not part of the same protein in its natural state. Examples of fusion proteins include a DNase I variant fused to an SSO7d DNA binding peptide (see for example, U.S. Pat. No. 6,627,424), a transcription factor (see for example, U.S. Pat. No. 10,041,051), an antibody, protein A (e.g., SpA), a binding domain suitable for immobilization such as maltose binding domain (MBP), a histidine tag ("His-tag"; e.g., SEQ ID NOS:4-8), chitin binding domain (e.g., SEQ ID NO:7), alpha mating factor (e.g., SEQ ID NO:8) or a SNAP-Tag® (New England Biolabs, Ipswich, MA (see for example U.S. Pat. Nos. 7,939,284 and 7,888,090)), and/or albumin. The binding peptide may be used to improve solubility or yield of the DNase I variant during the production of the protein reagent. Other examples of fusion proteins include fusions of a DNase I and a heterologous targeting sequence, a linker, an epitope tag, a detectable fusion partner, such as a fluorescent protein, β-galactosidase, luciferase and/or functionally similar peptides. Components of a fusion protein may be joined by one more peptide bonds, disulfide linkages, and/or other covalent bonds.

As used herein, "non-naturally occurring" refers to a polynucleotide, polypeptide, carbohydrate, lipid, or composition that does not exist in nature. Such a polynucleotide, polypeptide, carbohydrate, lipid, or composition may differ from naturally occurring polynucleotides polypeptides, carbohydrates, lipids, or compositions in one or more respects. For example, a polymer (e.g., a polynucleotide, polypeptide, or carbohydrate) may differ in the kind and arrangement of the component building blocks (e.g., nucleotide sequence, amino acid sequence, or sugar molecules). A polymer may differ from a naturally occurring polymer with respect to the molecule(s) to which it is linked. For example, a "non-naturally occurring" protein may differ from naturally occurring proteins in its secondary, tertiary, or quaternary structure, by having a chemical bond (e.g., a covalent bond including a peptide bond, a phosphate bond, a disulfide bond, an ester bond, and ether bond, and others) to a polypeptide (e.g., a fusion protein), a lipid, a carbohydrate, or any other molecule. Similarly, a "non-naturally occurring" polynucleotide or nucleic acid may contain one or more other modifications (e.g., an added label or other moiety) to the 5'-end, the 3' end, and/or between the 5'- and 3'-ends (e.g., methylation) of the nucleic acid. A "non-naturally occurring" composition may differ from naturally occurring compositions in one or more of the following respects: (a) having components that are not combined in nature, (b) having components in concentrations not found in nature, (c) omitting one or more components otherwise found in naturally occurring compositions, (d) having a form not found in nature, e.g., dried, freeze dried, crystalline, aqueous, and (e) having one or more additional components beyond those found in nature (e.g., buffering agents, a detergent, a dye, a solvent or a preservative).

With reference to an amino acid, "position" refers to the place such amino acid occupies in the primary sequence of a peptide or polypeptide numbered from its amino terminus to its carboxy terminus. A position in one primary sequence may correspond to a position in a second primary sequence, for example, where the two positions are opposite one another when the two primary sequences are aligned using an alignment algorithm (e.g., BLAST (Journal of Molecular Biology. 215 (3): 403-410) using default parameters (e.g., expect threshold 0.05, word size 3, max matches in a query range 0, matrix BLOSUM62, Gap existence 11 extension 1, and conditional compositional score matrix adjustment) or custom parameters). An amino acid position in one sequence may correspond to a position within a functionally equivalent motif or structural motif that can be identified within one or more other sequence(s) in a database by alignment of the motifs.

As used herein, "salt indifferent" refers to a property or capacity to display activity both in the absence of salt and across a range of concentrations of one or more salts. A salt indifferent DNase I variant, for example, may display DNA-binding activity and/or catalytic activity in the absence or presence of one or more salts (e.g., from 0 mM to 300 mM salt) that is at least 20%, at least 25%, at least 30%, at least 35%, at least 40%, at least 45%, at least 50%, at least 55%, or at least 60% of such variant's peak activity. For example, DNase I variant V7 S43K S206K has at least 20% of its peak catalytic activity under conditions spanning a range of total salt from 0 mM NaCl to 300 mM. Salt indifferent enzymes may be distinguished from salt sensitive enzymes, which have little or no activity (e.g., less than 20% of peak catalytic activity) in the absence of salt (salt-requiring enzymes) or have little or no activity (e.g., less than 20% of peak catalytic activity) in the presence of salt (salt-labile enzymes).

As used herein, "salt tolerant" refers to a property or capacity to display activity in the presence of one or more salts. A salt tolerant DNase I variant, for example, may display DNA-binding activity and/or catalytic activity in the presence of one or more salts. Binding activity may be evaluated in suitable biochemical terms, for example, binding affinity (Kd). Similarly, catalytic activity may be evaluated in suitable biochemical terms, for example, Michaelis constant (Km) and/or maximal reaction velocity (Vmax). Catalytic activity and/or DNA binding of a salt tolerant DNase I variant may be less sensitive to the presence of salt than a reference enzyme (e.g., a corresponding wild-type enzyme). A salt tolerant DNase I variant, for example, may bind a double stranded polydeoxyribonucleic acid and/or hydrolyze one or more polydeoxyribonucleic acid substrates to yield products comprising at least one 5'-phosphorylated polydeoxyribonucleotide and/or at least one 3'-hydroxylated polydeoxyribonucleotide in the presence of at least 50 mM, at least 100 mM, at least 150 mM, at least 200 mM, at least 250 mM, or at least 300 mM salt. Catalytic activity of a salt tolerant DNase I variant in the presence of 200 mM salt may be at least 50%, at least 60%, at least 70%, at least 80%, at least 90%, at least 95%, or at least 98% of the activity of the same salt tolerant DNase I variant in the absence of salt when assayed by any method disclosed herein. A salt tolerant DNase I variant in the presence of 200 mM salt may bind double stranded DNA with a dissociation constant (Kd) that is less than 10×, less than 5×, less than 2×, less that 0.5×, less that 0.25×, or less than 0.1× greater than the dissociation constant the same salt tolerant DNase I variant in the absence of salt when assayed by any method disclosed herein. A salt tolerant DNase I variant may display at least 20%, at least 22%, at least 24%, at least 26%, at least 28%, at least 30%, at least 35%, at least 40%, or at least 50% of its peak catalytic activity in the presence of up to 300 mM salt. In the context of salt tolerance and salt indifference, a salt may be a monovalent salt (e.g., NaCl), a divalent salt (e.g., $MgCl_2$, $CaCl_2$), an organic salt ($NaCH_3COO$), and/or an inorganic salt.

As used herein, "substitution" at a position in a subject amino acid sequence refers to any difference at that position relative to the corresponding position in a reference sequence, including a deletion, an insertion, and a different amino acid, where the subject and reference sequences are otherwise at least 80% identical to each other. A substitution in a subject sequence, in addition to being different than the reference sequence, may differ from all corresponding positions in naturally occurring sequences that are at least 80% identical to the subject sequence. A substitution may be represented by a letter followed by a number, for example, E13, which indicates the position of the subject sequence corresponding to position 13 of the reference sequence and comprises an insertion, a deletion, or any amino acid other than glutamate. A substitution may be represented by a letter followed by a number followed by another letter, for example, E13K, which indicates the position 13 of the reference sequence is glutamate and the position of the subject sequence corresponding to position 13 of the reference sequence is lysine, not glutamate.

All publications, patents, and patent applications mentioned in this specification are herein incorporated by reference to the same extent as if each individual publication, patent, or patent application was specifically and individually indicated to be incorporated by reference. All reagents referenced, if unavailable elsewhere, may be obtained from the indicated source and/or New England Biolabs, Inc. (Ipswich, MA).

Compositions

The present disclosure relates, in some embodiments, to compositions comprising a DNase I variant. DNase I variants, in some embodiments, may have one or more other desirable properties including, for example, reduced binding affinity to actin, mucolytic activity, and/or phosphodiesterase/hydrolytic activity. DNase I variant compositions may comprise (a) a DNase I substrate, including, for example, a double stranded DNA, a polynucleotide comprising DNA and RNA, a fluorescent probe (e.g., FIG. 1), and (b) a DNase I variant. DNase I variant compositions may comprise, in some embodiments, a DNase I variant, a DNase substrate, a salt (e.g., NaCl, $MgCl_2$), a protein (e.g., albumin, topoisomerase, polymerase), DNA, RNA, a buffering agent, a cell (e.g., intact or digested), a biological fluid or secretion (e.g., mucus, pus), and/or (non-naturally occurring) combinations thereof. A DNase I variant composition may comprise, for example, a DNase I variant (e.g., having an amino acid sequence at least 85% identical to SEQ ID NO:1 and comprises one or more substitutions at positions corresponding to SEQ ID NO:1, the substitutions and corresponding positions selected from E13K, E13R, N18A, A35V, S43K, S43R, H44K, H44R, N74K, N74R, S75K, S75R, P103S, N106A, T205K, T205R, S206K, S206R, T207K, and T207R) and at least 10 mM salt, at least 25 mM salt, at least 50 mM salt, at least 100 mM salt, at least 150 mM salt, at least 200 mM salt, at least 250 mM salt, at least 300 mM salt, and/or at least 350 mM salt. In each case, salt present may be a single salt species or a mixture of salts. In each case, salt present may comprise monovalent and/or divalent salts. A DNase I variant composition may comprise one or more ionic, non-ionic, and/or zwitterionic detergents (e.g., octoxinol, polysorbate 20), crowding agents, sugars, starches, cellulose, lipids, and oils.

DNase I variants and compositions thereof may have any desirable form including, for example, a liquid, a gel, a film, a powder, a cake, and/or any dried or lyophilized form. A DNase I variant composition may comprise one or more stabilizers including, for example, an aptamer, a monosaccharide, a disaccharide, a trisaccharide, a tetrasaccharide, starch, cellulose, dextrin, and dextran.

In some embodiments, a DNase I variant may be encoded by a nucleic acid sequence having at least 80%, at least 85%, at least 90%, at least 93%, at least 96%, at least 97%, at least 98% or at least 99% identity to a sequence (e.g., a codon optimized sequence) encoding the amino acid sequence of SEQ ID NO: 1, 5, 6, 7, 8, 9, 10, and/or 11. For example, a DNase I variant may be encoded by a nucleic acid sequence having at least 80%, at least 85%, at least 90%, at least 93%, at least 96%, at least 97%, at least 98% or at least 99% identity to nucleotides 1-780 of SEQ ID NO: 4. A nucleic acid encoding a DNase I variant may be included in an expression cassette, expression vector, or other expressible form suitable for in vitro or in vivo expression (e.g., in *E. coli* or other bacteria or *P. pastoris* or other yeast).

Methods

DNase I variants disclosed herein may be useful in many molecular, cellular, and therapeutic applications, processes, methods, and/or workflows. For example, DNase I variants may be use in methods and/or workflows that include, for example, strand displacement, nick translation, in vitro transcription, DNA fragmentation, footprinting, PCR (e.g., RT-PCR), RNA sequencing, and RNA purification. DNase I variants may be used, in some embodiments, to digest DNA (e.g., double-stranded DNA) where its presence may impair or complicate analysis (e.g., of other components of a sample). The present disclosure provides, in some embodiments, methods comprising contacting a DNase I variant with a molecule comprising a polydeoxyribonucleotide. For example, a method may comprise contacting a DNase I variant with a composition comprising DNA and at least one non-DNA species to digest the DNA present. Such action on the DNA present may leave the non-DNA species unmodified or substantially unmodified (e.g., as to structure, composition, and/or concentration).

The present disclosure relates, in some embodiments, to methods comprising contacting a DNase I variant with a composition comprising DNA and RNA to digest the DNA molecules present without modifying the RNA. Such contacting may be included in methods for cleaning up RNA after isolation from a cell or tissue, after in vitro transcription, prior to elution from a solid support, and/or prior to RT-PCR. The RNA may remain unaltered or substantially unaltered. For example, contacting a DNase I variant with a composition comprising DNA and RNA may result in a product composition comprising over 50%, over 80%, over 85%, over 90%, over 95%, or over 99% of the starting, intact RNA and/or less than 50%, less than 25%, less than 10%, less than 5%, less than 1%, less than 0.5%, or less than 0.1% of the starting, intact DNA. A method may include fracturing one or more cells to form the composition comprising DNA and RNA, wherein at least a portion of the DNA comprises cellular DNA and at least a portion of the RNA comprises cellular RNA. The size of digestion products and/or degree of digestion may be managed, for example, by selecting the DNase I variant with a desired activity, increasing or decreasing the concentration of the selected DNase I variant, increasing or decreasing the incubation time or temperature, increasing or decreasing magnesium concentration and/or increasing or decreasing salt concentration. In some embodiments, methods may be adapted to digest DNA as fully as practicable or digest DNA (non-specifically) into fragments within a selected range of sizes.

The present disclosure relates, in some embodiments, to methods comprising contacting a DNase I variant with a composition comprising DNA and a protein (or another non-DNA molecule of interest) to digest the DNA molecules present without modifying the protein (or another non-DNA molecule of interest). Such contacting may be included in methods for cleaning up protein after isolation from a cell or tissue, preparing protein samples for separation on 2-D gels, and/or identifying protein binding sequences on DNA (DNase I footprinting). The RNA may remain unaltered or substantially unaltered. For example, contacting a DNase I variant with a composition comprising DNA and a protein (or another non-DNA molecule of interest) may result in a product composition comprising over 50%, over 80%, over 85%, over 90%, over 95%, or over 99% of the starting, intact protein (or another non-DNA molecule of interest) and/or less than 50%, less than 25%, less than 10%, less than 5%, less than 1%, less than 0.5%, or less than 0.1% of the starting, intact DNA. A method may include fracturing one or more cells to form the composition comprising DNA and protein (or another non-DNA molecule of interest), wherein at least a portion of the DNA comprises cellular DNA and at least a portion of the protein (or another non-DNA molecule of interest) comprises cellular protein (or another cellular, non-DNA molecule of interest).

In some embodiments, a DNase I variant may be contacted with a composition comprising DNA (e.g., genomic fragments or other long (≥10 kb) DNA fragments) to digest such DNA. Such contacting may be included in methods for creating a fragmented DNA library and methods of cell culture preparation (e.g., tissue disaggregation), cultivation, manipulation, and storage to reduce or prevent cell clumping.

A DNase I variant may be used in connection with in vitro transcription (IVT), according to some embodiments. IVT methods may include contacting a DNA template (e.g., a double stranded DNA comprising a coding sequence and an expression control sequence operably linked to the coding sequence) with an RNA polymerase (e.g., T7 RNA polymerase) optionally in the presence of NTPs, salt, and/or a reaction buffer to form a transcription product composition comprising a transcription product (e.g., RNA) and the DNA template. IVT methods, in some embodiments, may comprise contacting a DNase I variant with the DNA template to digest the DNA template and form a digested composition comprising DNA template digestion products. IVT methods may comprise separating the transcription product from one or more of the other components of the transcription product composition or the digested composition, for example, the DNA template, DNA template digestion products, the RNA polymerase, NTPs, salt, and reaction buffer. Techniques for such separation include column purification, phase separation (e.g., phenol-chloroform), and fractionation (e.g., size, charge, hydrophobicity, polarity, and ratios thereof) among others.

A method may include transcribing a DNA template to form the composition comprising DNA and RNA, wherein at least a portion of the DNA comprises the DNA template and at least a portion of the RNA comprises RNA arising from the transcription. A method may comprise contacting a DNase I variant with a composition comprising DNA and RNA to produce a product solution comprising RNA and optionally less than 5%, less than 4%, less than 3%, less than 2%, less than 1%, less than 0.5% of the DNA in the starting composition.

The amount of transcription product (RNA) remaining after contact with the DNase I variant may be assessed by available methods including, for example, RT-qPCR. The amount of DNA template remaining after contact with the DNase I variant may be assessed by available methods including, for example, qPCR.

According to some embodiments, contacting a polydeoxyribonucleic acid (e.g., the template DNA for IVT) with a DNase I variant may (further) comprise contacting the polydeoxyribonucleic acid with the DNase I variant in the presence of at least 10 mM salt, at least 25 mM salt, at least 50 mM salt, at least 100 mM salt, at least 150 mM salt, at least 200 mM salt, at least 250 mM salt, at least 300 mM salt, and/or at least 350 mM salt. In each case, salt present may be a single salt species or a mixture of salts. In each case, salt present may comprise monovalent and/or divalent salts.

The present disclosure further relates to methods of making a DNase I variant. For example, a DNase I variant may be produced by in vitro transcription and/or in vitro translation (e.g., PURExpress®, New England Biolabs, Inc.). In some embodiments, a DNase I variant may be produced in vivo. For example, a method may include (a) culturing a host cell comprising an expression vector or expression cassette comprising a nucleic acid sequence having at least 80%, at least 85%, at least 90%, at least 93%, at least 96%, at least 97%, at least 98% or at least 99% identity to a sequence (e.g., a codon optimized sequence) encoding the amino acid sequence of SEQ ID NO: 1, 5, 6, 7, 8, 9, 10, and/or 11 operably linked to an expression control sequence to produce a cultured host cell composition comprising the DNase I variant, and (optionally) isolating the DNase I variant from the cultured host cell composition (e.g., culture supernatant, culture lysate, culture cell paste).

Kits

The present disclosure further relates to kits including DNase I variants. For example, a kit may include a DNase I variant and one or more of dNTPs, rNTPs, primers, other enzymes (e.g., polymerases), buffering agents, or combinations thereof. A DNase I variant may be included in a storage buffer (e.g., comprising a buffering agent and comprising or lacking glycerol). A kit may include a reaction buffer which may be in concentrated form, and the buffer may contain additives (e.g., glycerol), salt (e.g. KCl), reducing agent, EDTA or detergents, among others. A kit comprising dNTPs may include one, two, three or all four of dATP, dTTP, dGTP and dCTP. A kit comprising rNTPs may include one, two, three or all four of rATP, rUTP, rGTP and rCTP. A kit may further comprise one or more modified nucleotides. A kit may optionally comprise one or more primers (random primers, bump primers, exonuclease-resistant primers, chemically modified primers, custom sequence primers, or combinations thereof). One or more components of a kit may be included in one container for a single step reaction, or one or more components may be contained in one container, but separated from other components for sequential use or parallel use. The contents of a kit may be formulated for use in a desired method or process.

A kit is provided that contains: (i) a DNase I variant; and (ii) a buffer. A DNase I variant may be present in a dried or lyophilized form or may be included in a buffer (e.g., a storage buffer or a reaction buffer in concentrated form). A kit may contain a DNase I variant in a tube or mastermix suitable for receiving and transcribing a template nucleic acid. For example, a DNase I variant may be deposited in the cap of a tube while components for transcribing a template nucleic acid are deposited in the body of the tube. As desired, for example, upon completion of the transcription reaction, the tube may be tapped, shaken, turned, spun, or otherwise moved to contact the deposited DNase I variant with the transcription reaction mixture. A reaction buffer may include non-ionic, ionic (e.g. anionic or zwitterionic) surfactants and/or crowding agents. A kit may include a DNase I variant and the reaction buffer in a single tube or in different tubes and, if included in a single tube, the DNase I variant and the buffer may be present in the same or separate locations in the tube.

A subject kit may further include instructions for using the components of the kit to practice a desired method. The instructions may be recorded on a suitable recording medium. For example, instructions may be printed on a substrate, such as paper or plastic, etc. As such, the instructions may be present in the kits as a package insert, in the labeling of the container of the kit or components thereof (i.e., associated with the packaging or sub-packaging) etc. Instructions may be present as an electronic storage data file residing on a suitable computer readable storage medium (e.g. a CD-ROM, a flash drive). Instructions may be provided remotely using, for example, cloud or internet resources with a link or other access instructions provided in or with a kit.

EXAMPLES

Some specific example embodiments may be illustrated by one or more of the examples provided herein.

Example 1: Catalytic Activity Assay

Catalytic activity of a commercially available maltose binding protein—WT DNase I fusion (New England Biolabs, Inc. #M0303) and DNase I variants were assayed using a quenched fluorescent, dsDNA probe comprising a 5' FAM (fluorescein) label and a 3' Iowa black fluorescence quencher ("IA Bq FQ"). When the probe is heated to 95° C. and then gradually cooled, it folds into a hairpin structure (FIG. 1) in which the fluorescent signal is quenched. Upon cleavage, the FAM fluorophore may separate from the Iowa black quencher to produce a fluorescent signal that can be measured at 517 nm using a spectrophotometer.

Screening reactions contained 3 µM probe in a 30 µl reaction and were carried out in black half-area 96-well plates (costar 3694). Screening reactions were performed at ambient temperature (23±3° C.) in DNase I buffer (comprising 10 mM Tris pH 7.6, 2.5 mM $MgCl_2$, 0.5 mM $CaCl_2$) with and without 200 mM NaCl. DNA cleavage was monitored for 2 minutes using a Spectramax M5 spectrophotometer, and initial rates were calculated from the linear portion of the graph (~60 seconds).

Alternatively, screening reactions containing 5 µM probe in a 50 µl reaction were run at 30±2° C. for 2 minutes. Rates were calculated from 50 s to 100 s portion of the graph.

Example 2: In Vitro Synthesis of DNase I Variants

Selected DNase I variants were synthesized using PURExpress®. Wild-type (WT) bovine DNase I was cloned into a modified version of pET28 lacking a promoter. The V7 sequence (SEQ ID NO:1), having 16 single variations from the naturally occurring bovine sequence (SEQ ID NO:3), was cloned into the same vector. Single, double, triple, and quadruple variations were introduced into the V7 DNase I backbone (SEQ ID NO:1) including E13K, E13R, S43K, S43R, H44K, H44R, N74K, N74R, S75K, S75R, T205K, T205R, S206K, S206R, T207K, T207R, E13K S43K, E13K N74R, E13K S206K, E13K T207R, S43K N74R, S43K S206K, S43K T207R, N74R S206K, N74R T207R, S206K T207R, A35V S43K T207R, S43K P103S T207R, A35V N74R T207R, N74R P103S T207R, A35V N74R P103S T207R. DNase I variants were amplified by PCR using a 5' primer containing a consensus T7 promoter. Proteins were then synthesized in vitro using the NEB HiScribe™ in vitro transcription kit followed by the PURExpress® in vitro transcription/translation kit in accordance with the manufacturer's instructions (New England Biolabs, Inc., Ipswich, MA).

Example 3: Synthesis of DNase I Variants in Yeast

Selected DNase I variants were cloned into plasmid pD912(GAP) under the control of the constitutive GAP promoter, with an N-terminal alpha-mating factor secretion signal and C-terminal His6 tag (SEQ ID NO:8). Single, double, triple, and quadruple variations were introduced into the V7 DNase I backbone (SEQ ID NO:1) including E13K, E13R, S43K, S43R, H44K, H44R, N74K, N74R, S75K, S75R, T205K, T205R, S206K, S206R, T207K, T207R, E13K S43K, E13K N74R, E13K S206K, E13K T207R, S43K N74R, S43K S206K, S43K T207R, N74R S206K, N74R T207R, S206K T207R, A35V S43K T207R, S43K P103S T207R, A35V N74R T207R, N74R P103S T207R, A35V N74R P103S T207R. The plasmids were then linearized and integrated into the genome of Pichia pastoris MutS. Strains were grown for 48 h in buffered complex glycerol (BMGY) medium, and culture supernatants were collected by centrifugation. Size fractionation of the products suggest the DNase I produced may be glycosylated. The parental Pichia pastoris supernatants had no background activity with the FAM hairpin DNA probe (FIG. 1).

Example 4: Catalytic Activity of DNase I Variants

Figure 3A:
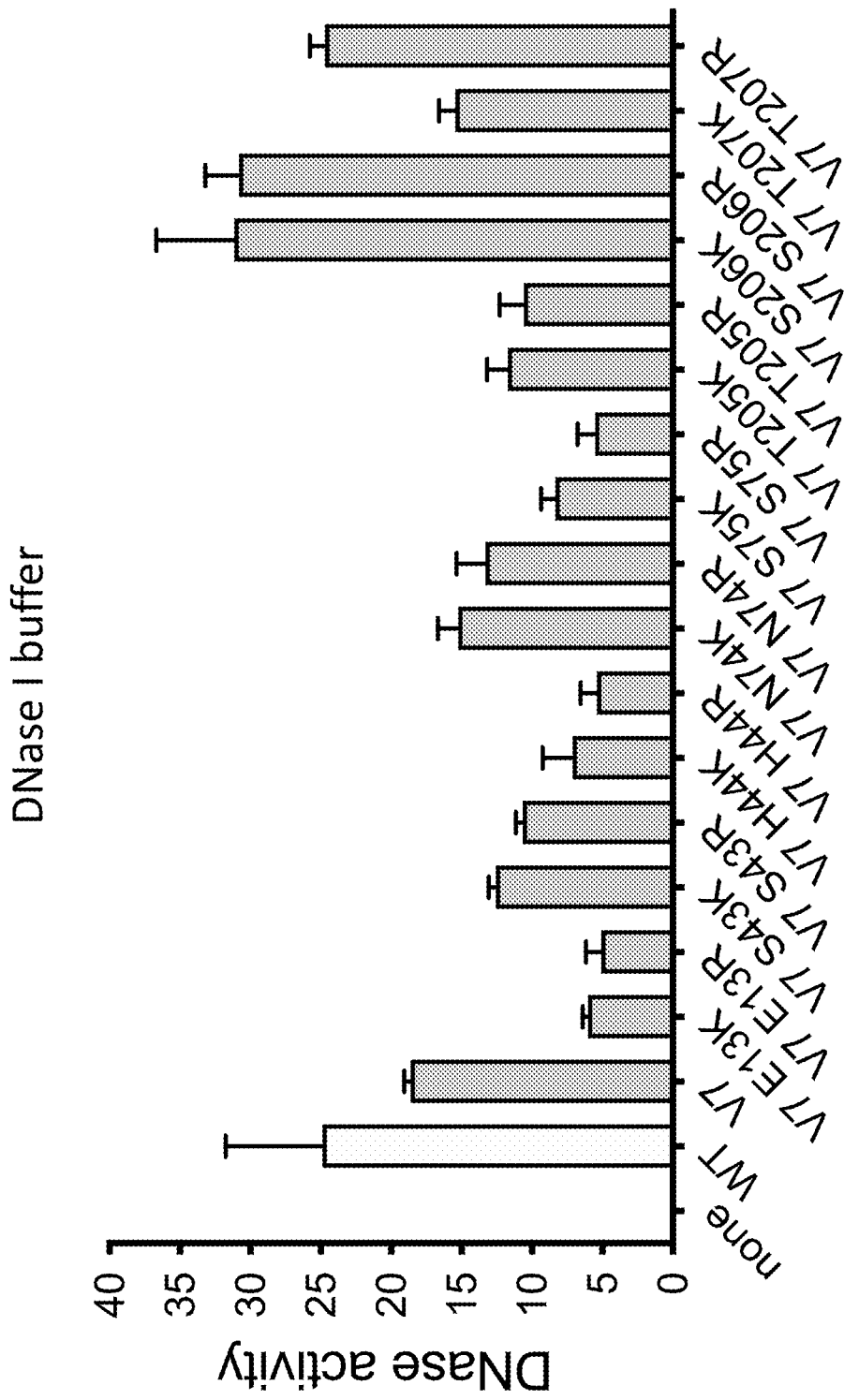
FIG. 3A shows DNase activity of wild type, V7, and single lysine/arginine variants in DNase I buffer comprising 10 mM Tris pH 7.6, 2.5 mM $MgCl_2$, 0.5 mM $CaCl_2$.
Figure 3B:
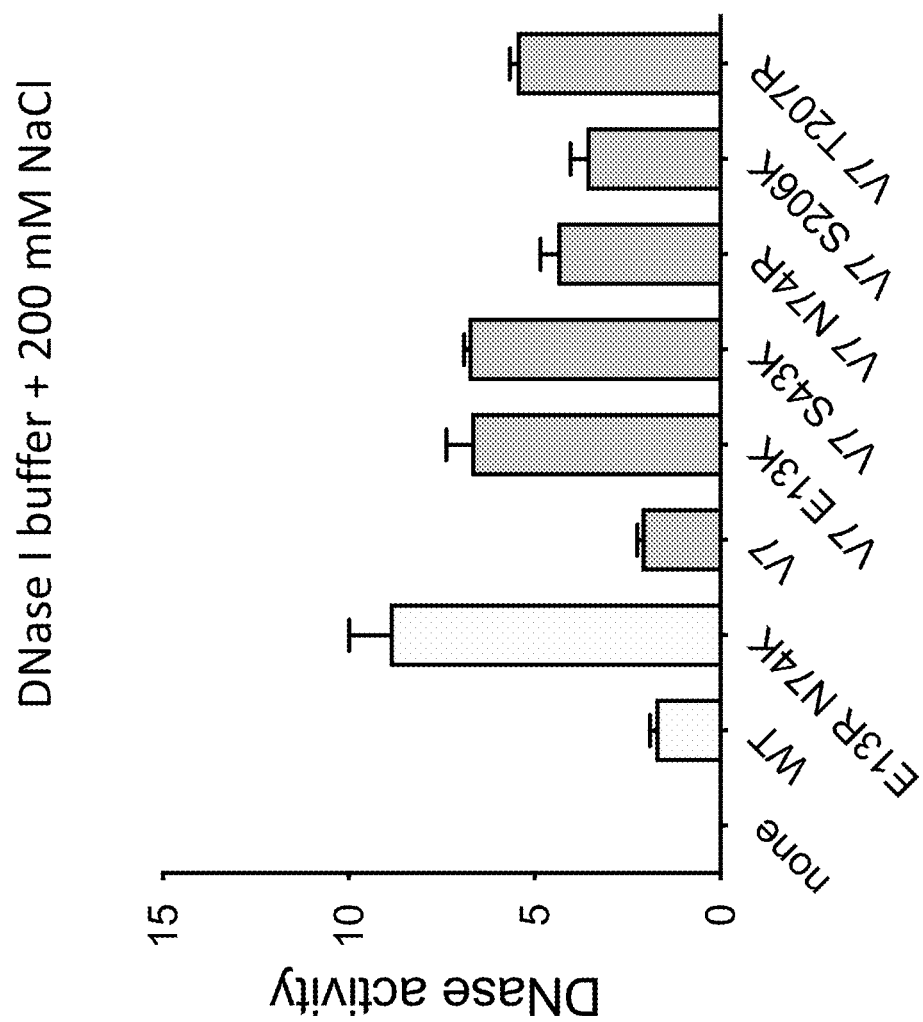
FIG. 3B shows DNase activity of wild type, V7, and single lysine/arginine variants in DNase I buffer comprising 10 mM Tris pH 7.6, 2.5 mM $MgCl_2$, 0.5 mM $CaCl_2$, 200 mM NaCl.
Figure 3C:
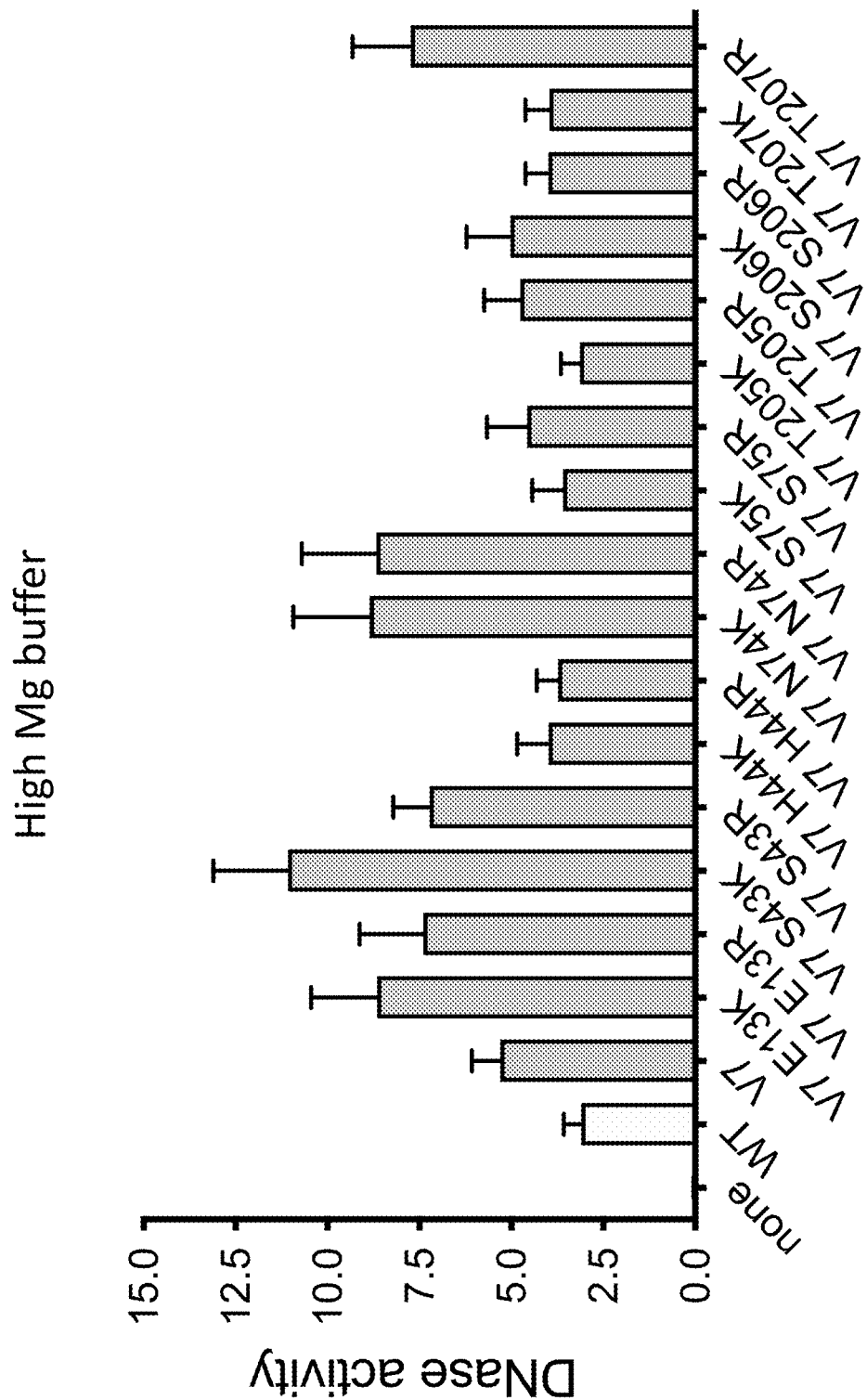
FIG. 3C shows DNase activity of wild type, V7, and single lysine/arginine variants in a high-$Mg^{2+}$ buffer comprising 10 mM Tris pH 7.5, 10 mM NaCl, 40 mM $MgCl_2$.
Figure 4A:
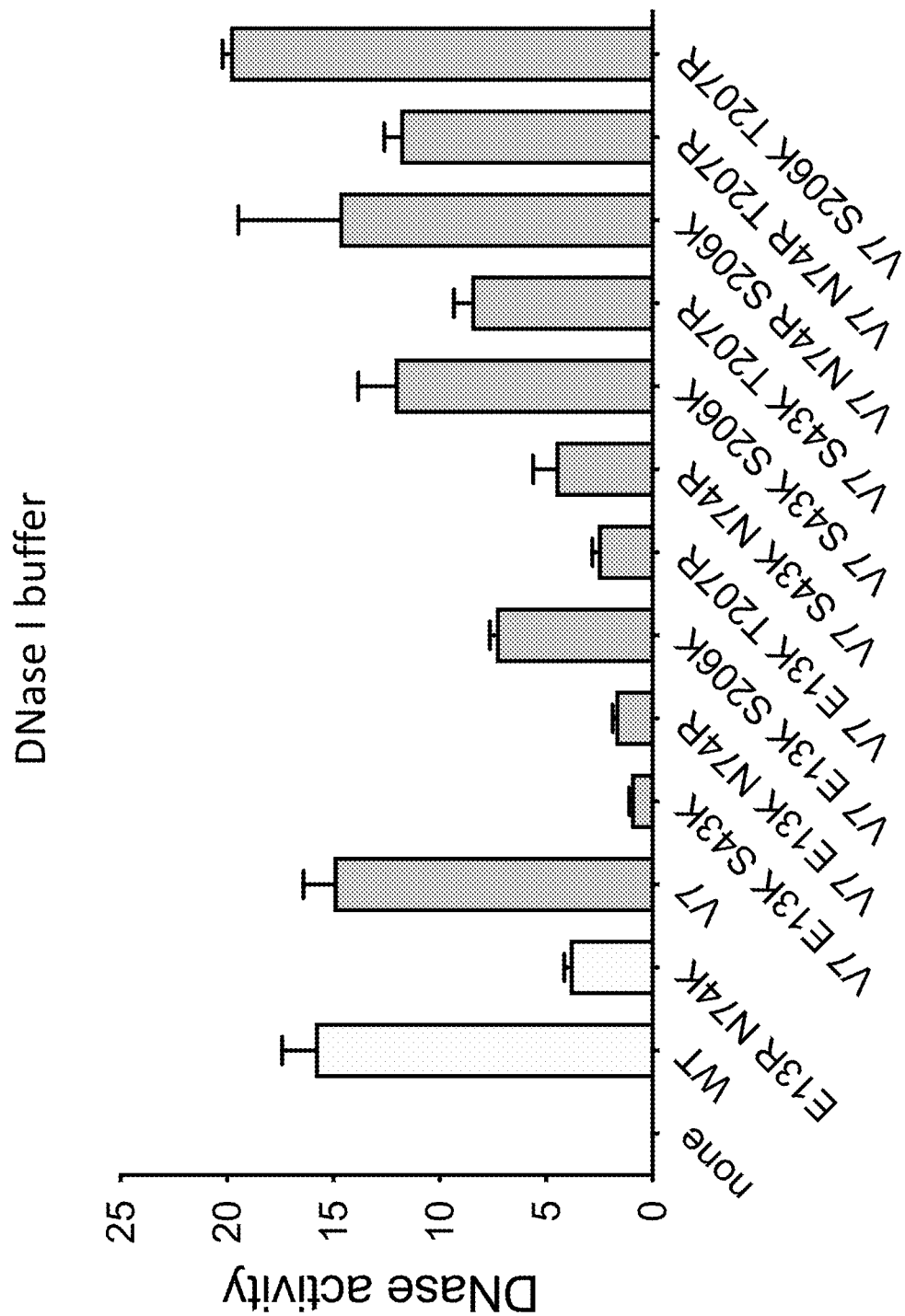
FIGS. 4A-4C show DNase I activity of V7 and lysine/arginine double mutants relative to wild-type. "WT" refers to wild type bovine DNase I. The variant marked "E13R N74K" has the wild type bovine DNase I sequence with the two indicated substitutions. All other variants (gray bars) have the V7 sequence with the indicated substitutions.
Figure 4B:
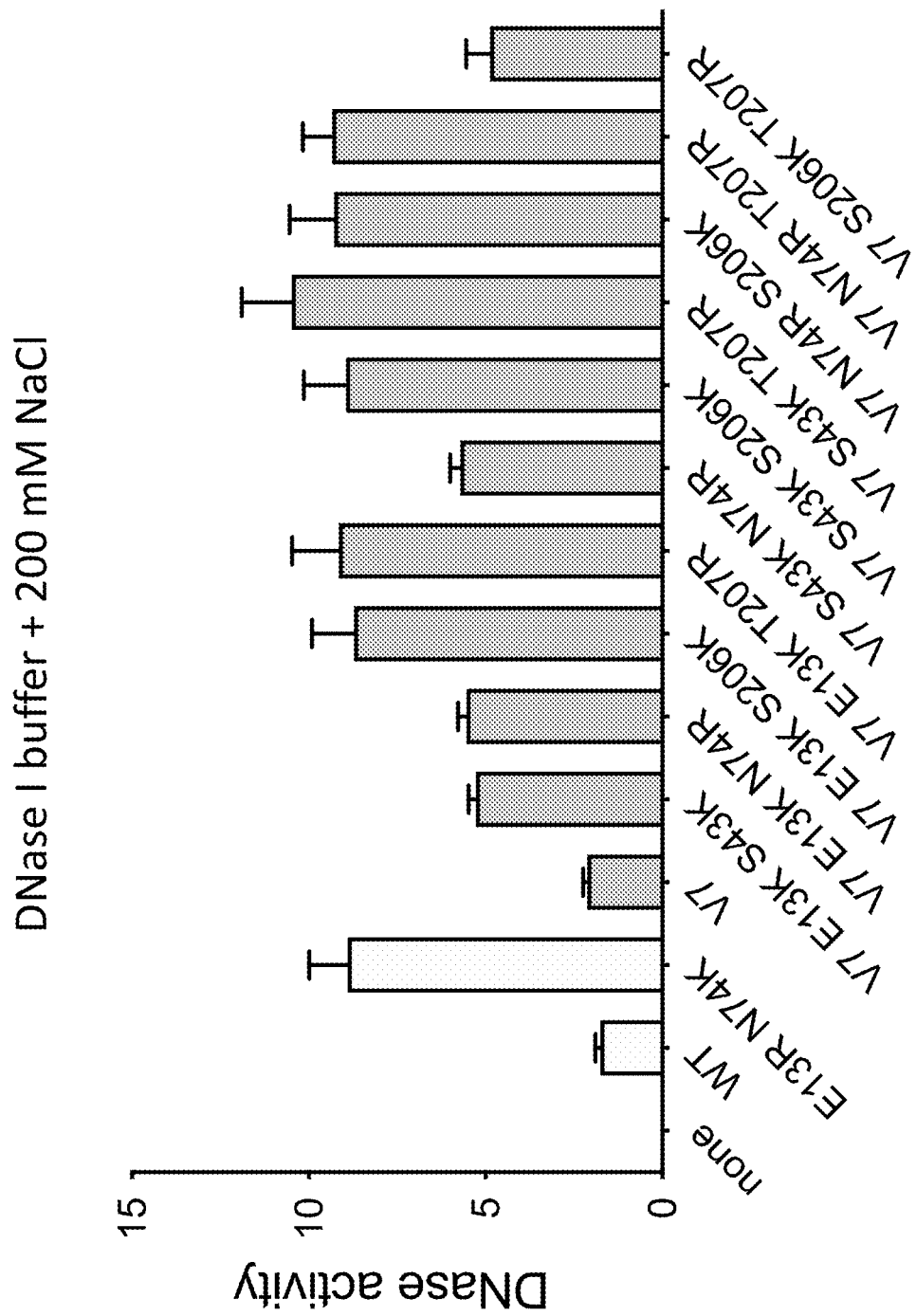
Figure 4C:
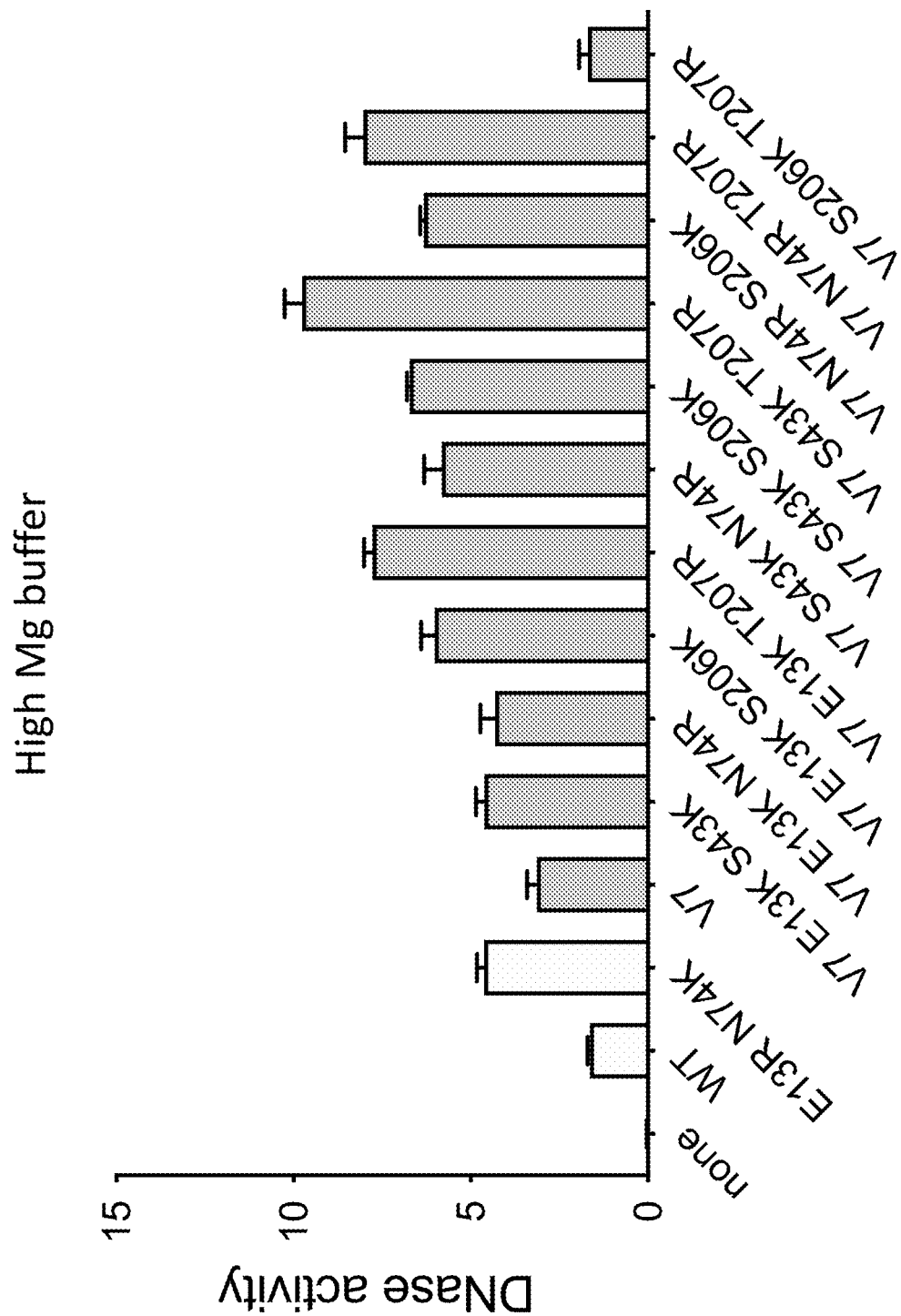

Catalytic activity of bovine DNase I ("WT"; SEQ ID NO:3 produced according to Example 2) and DNase I variants were assayed in accordance with Example 1. PURExpress® reactions (Example 2) or Pichia culture supernatants (Example 3) each were diluted 100-fold in DNase I buffer comprising 10 mM Tris pH 7.6, 2.5 mM $MgCl_2$, 0.5 mM $CaCl_2$ with or without NaCl or in a high-$Mg^{2+}$ buffer comprising 10 mM Tris pH 7.5, 10 mM NaCl, 40 mM $MgCl_2$. Activity of DNase I variants having single amino acid substitutions and produced in vitro are shown in FIGS. 3A (DNase I buffer), 3B (DNase I buffer+200 mM NaCl), and 3C (high-$Mg^{2+}$ buffer) with variants displaying from 20% to 380% of the activity of bovine DNase I. Activity of DNase I variants having two amino acid substitutions and produced in vitro are shown in FIGS. 4A (DNase I buffer), 4B (DNase I buffer+200 mM NaCl), and 4C (high-$Mg^{2+}$ buffer) with variants displaying from 7% to 600% of the activity of bovine DNase I.

Figure 5:
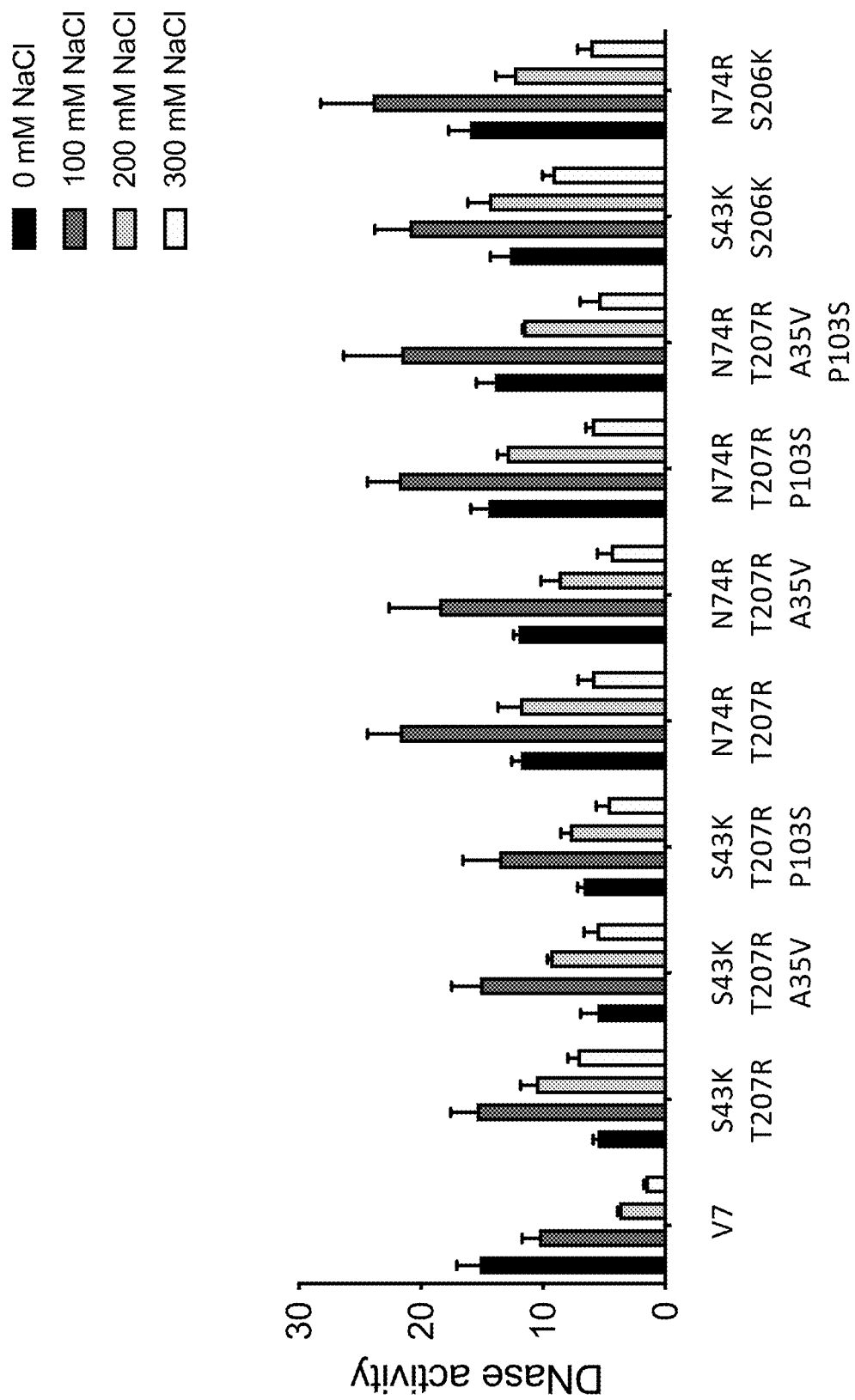
FIG. 5 shows the activity of variants having the sequence of V7 with the indicated double or triple substitutions indicated. Activity was measured in DNase I buffer with either 0 mM, 100 mM, 200 mM, or 300 mM NaCl added.

DNase activities of variants with two, three, or four amino acid substitutions and produced in Pichia were tested in the presence of increasing concentrations of NaCl. Results are shown in FIG. 5 with all double, triple, and quadruple variants showing greater salt tolerance than variant V7.

Catalytic activity of equimolar concentrations of purified Bovine DNase I (e.g., #M0303, NEB) and DNase I variant V7 S43K S206K was assessed in DNase I buffer in the presence of increasing concentrations of NaCl using the FAM hairpin DNA probe as described in Example 1 with results shown in Table 1. Reactions contained 5 µM probe in a 50 µl reaction and were carried out at 30° C. in black half-area 96-well plates (costar 3694). DNA cleavage was monitored for 2 minutes using a Spectramax M3 spectrophotometer, and initial rates were calculated from the linear portion of the graph (~60 seconds).

The DNase I variant V7 S43K S206K displays an increase in catalytic activity at salt concentrations above 50 mM as compared to Bovine DNase I. Notably, while Bovine DNase I displays essentially no activity at salt concentrations >200 mM, under the conditions tested, the DNase I variant V7 S43K S206K still retains over 30% of its peak activity in the presence of 300 mM salt and retains over 10% of its peak activity in the presence of 400 mM salt.

TABLE 1

| [NaCl] (mM) | Bovine DNase I | V7 S43K/ S206K | Fold Improvement* |
|---|---|---|---|
| 0 | 10.44 ± 0.67 | 7.21 ± 0.62 | 0.7 |
| 50 | 7.72 ± 0.41 | 10.14 ± 0.77 | 1.3 |

TABLE 1-continued

| [NaCl] (mM) | Bovine DNase I | V7 S43K/ S206K | Fold Improvement* |
|---|---|---|---|
| 100 | 3.17 ± 0.20 | 12.02 ± 0.70 | 3.8 |
| 200 | 0.35 ± 0.04 | 7.34 ± 0.32 | 21.0 |
| 300 | 0.08 ± 0.03 | 3.84 ± 0.23 | 48.0 |
| 400 | 0.02 ± 0.02 | 1.33 ± 0.05 | 66.5 |
| 500 | 0.00 ± 0.01 | 0.64 ± 0.07 | ND** |

*Fold improvement of V7 S43K S206K:Bovine DNase I
**Not determined since bovine DNase I activity was 0.00.

Results were further confirmed by a second assay in which plasmid DNA was digested with DNase I (e.g., #M0303, NEB) or DNase I variants and reaction products were fractionated on gels. Consistent with the FAM hairpin DNA probe results, DNase I showed lower activity at NaCl concentrations of 50 mM and above while DNase I variants digest substrate DNA at concentrations of 50 mM, 100 mM, and 200 mM NaCl.

Example 5: Kinetics of DNase I Variants

Relative activities of DNase I variant V7 S43K S206K produced in vitro, a commercially available bovine DNase I (#M0303, NEB), and a variant of bovine DNase I, TURBO™ DNase (Thermo Fisher Scientific, Inc., Waltham, Massachusetts) were assessed in the presence of increasing concentrations of sodium chloride using the FAM hairpin DNA probe as described in Example 1. Catalytic activity was assessed in DNase I buffer to provide a buffer in which all three enzymes display activity and limit the number of potential variables. The manufacturer of TURBO™ DNase recommends using a different buffer, but the manufacturer has not publicly disclosed the composition of that recommended buffer.

Reactions contained 5 µM probe in a 50 µl reaction and were carried out at 30° C. in black half-area 96-well plates (costar 3694). DNA cleavage was monitored for 2 minutes using a Spectramax M3 spectrophotometer, and initial rates were calculated from the linear portion of the graph (~60 seconds). Results are shown in Table 2, in which activity is expressed as a percentage of the highest activity displayed for each enzyme.

TABLE 2

| Relative Activity | 0 mM NaCl | 50 mM NaCl | 100 mM NaCl |
|---|---|---|---|
| Bovine DNase | 100% | 74% | 30% |
| V7 S43K S206K | 60% | 84% | 100% |
| TURBO ™ DNase | 17% | 49% | 100% |

The DNase I variant V7 S43K S206K displays equivalent catalytic activity to TURBO™ DNase at a salt concentration of 100 mM under the conditions tested (which did not include the buffer recommended by TURBO™ DNase's manufacturer). As these data demonstrate, under the conditions tested, V7 S43K S206K displayed activity in the absence of salt, unlike TURBO™ DNase, and displayed salt tolerance over a wide range of salt concentrations. Most DNase I reactions are typically performed between 0-150 mM salt concentration. This data demonstrates the enhanced utility of the DNase I variant V7 S43K S206K compared to Bovine DNase I.

Example 6: In Vitro Transcription with DNase I Variants

RNA was transcribed from a Cluc DNA template (1 µg/µl) using HiScribe™ Quick High Yield RNA Synthesis Kit (New England Biolabs, Inc., Ipswich, MA). Synthesis reactions were allowed to proceed for 2 hours. Aliquots of 20 μL were treated with compositions (a) without DNase, (b) 4 U bovine DNase I (#M0303 (MBP fusion)), or (c) 2 U DNase I variant V7 S43K/S206K for 15 minutes at 37° C. RNA transcription products were purified from DNase I-treated samples using a Monarch® RNA Cleanup Kit (New England Biolabs, Inc., Ipswich, MA) and eluted in nuclease-free water (50 μl). Purified RNA was subjected to qPCR using a Luna® Universal Probe qPCR Master Mix (New England Biolabs, Inc., Ipswich, MA) to determine how much Cluc DNA template remained in such preparations, if any. Average Cq (quantification cycle) values for each sample were compared to a standard curve to determine the percent of residual, PCR-amplifiable DNA. Results are shown in TABLE 3.

TABLE 3

| DNase | None | M0303 (4 U) | V7 S43K/ S206K (2 U) |
|---|---|---|---|
| Average Cq | 8.83 | 19.77 | 21.26 |
| Residual DNA (ng) | 18.76 | 0.016 | 0.006 |
| % Residual DNA | 100% | 0.085% | 0.032% |
| Fold Improvement (per unit of enzyme) | N/A | N/A | 5.4 |

Example 7: Thermostability of DNase I Variants

Figure 6:
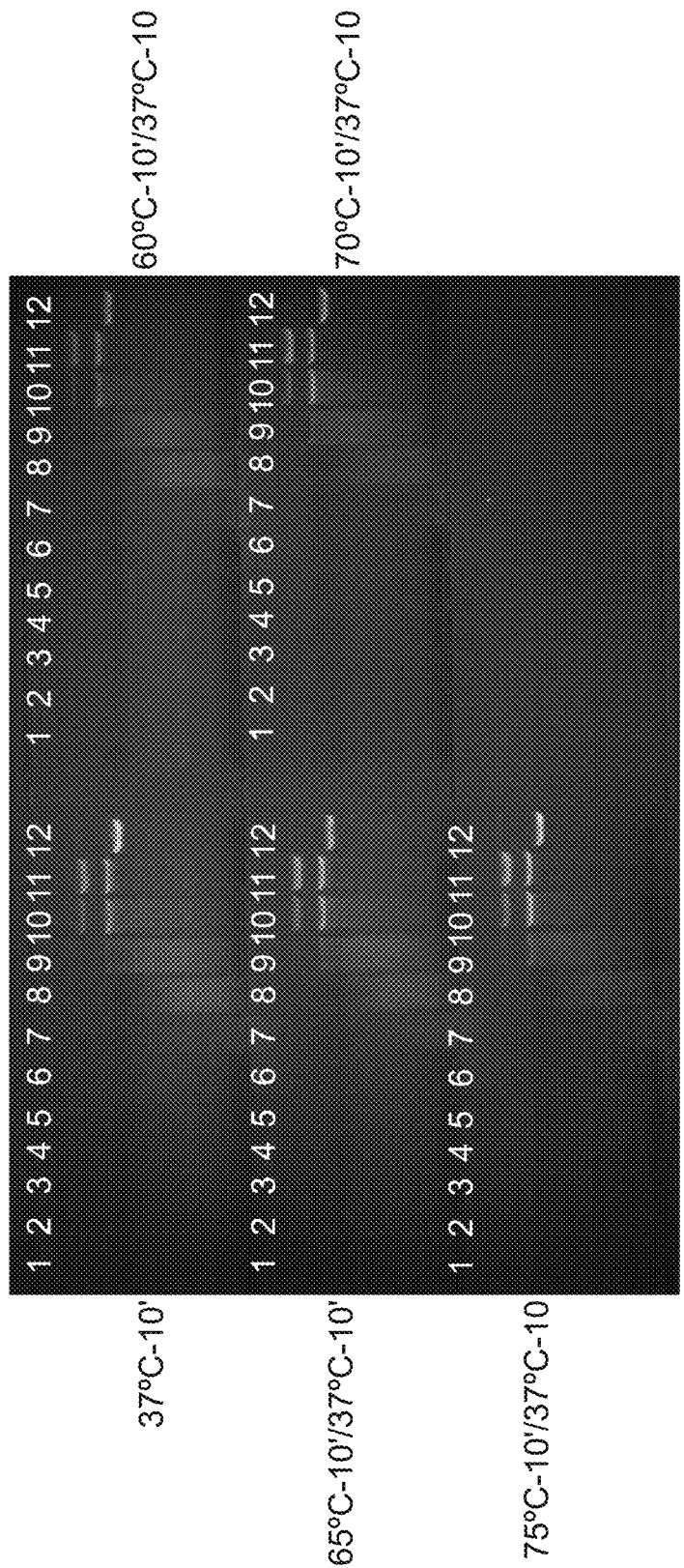
FIG. 6 shows the residual activity of the DNase I V7 S43K S206K at 37° C. after heat treatment up to 75° C. (for 10 minutes) prior to the addition of substrate (plasmid DNA). Activity was measured by visualizing reaction products fractionated on gels.

Thermotolerance was assessed by heating (60° C., 65° C., 70° C. or 75° C. for 10') the DNase I variant V7 S43K S206K in a 2-fold dilution series in reaction buffer containing 50 mM NaCl for 10 minutes before plasmid substrate (1 μg) was added and the samples then incubated for 37° C. (standard DNase reaction temperature) for 10 minutes. Reaction products were fractionated on gels as shown in FIG. 6. While the Bovine DNase I (#M0303 (MBP fusion)) is readily heat inactivated after 10 minutes at 75° C., the DNase I variant V7 S43K S206K retains 100% activity even after heat treatment at 75° C. for 10 minutes, demonstrating the enhanced thermotolerance of this enzyme.

Example 8: Specificity of DNase I Variants for DNA in DNA/RNA Hybrids

Figure 7:
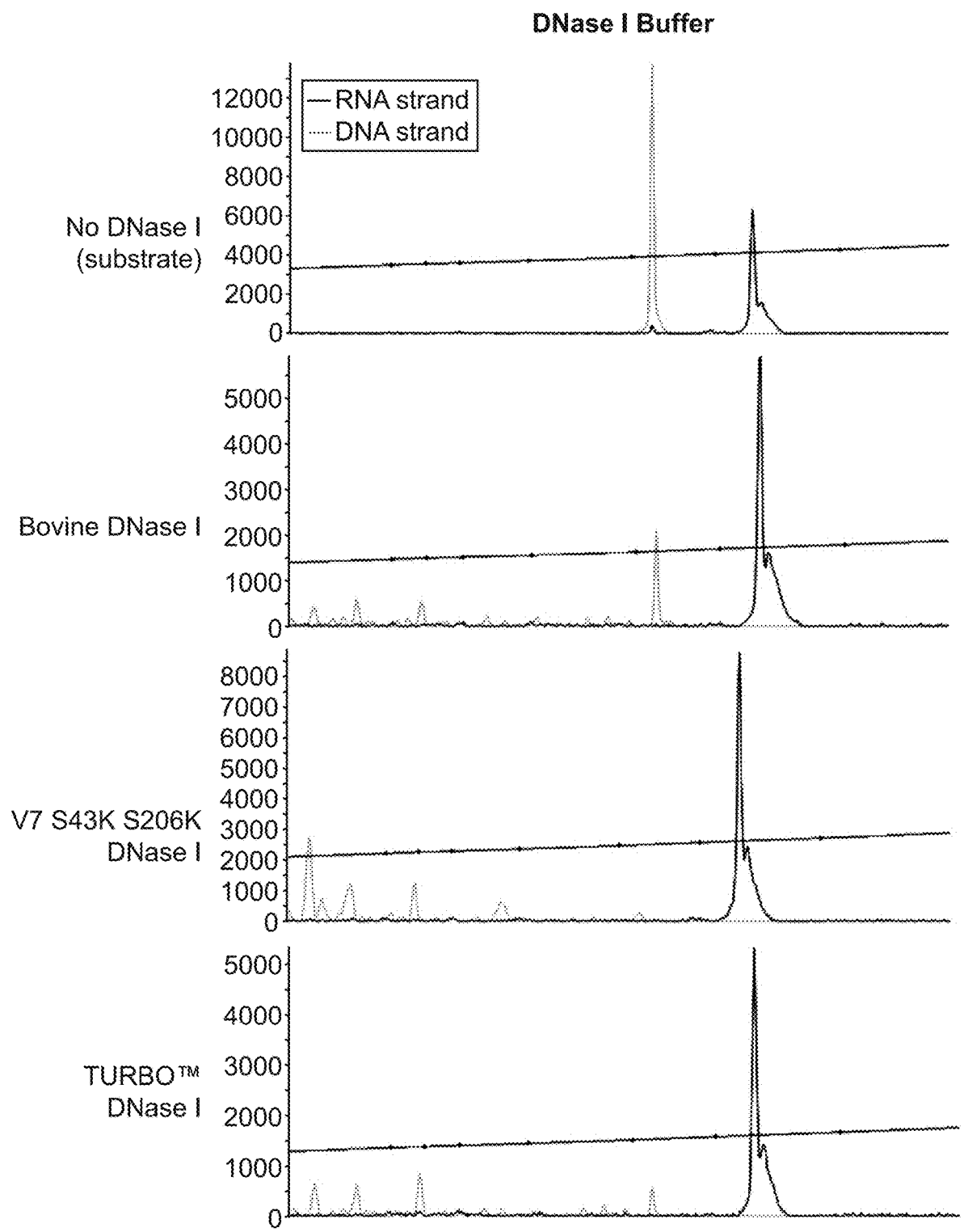
FIG. 7 show the ability of Bovine DNase I (NEB #M0303, MBP fusion), DNase I V7 S43K S206K and TURBO™ DNase to digest the DNA strand of a DNA/RNA hybrid. DNase was incubated with 20 pmol of a FAM-DNA/ROX-RNA hybrid (60 bp) for 10' at 37° C. in either DNase I reaction buffer (upper three panels) or TURBO™ DNase Reaction Buffer (bottom panel). Reaction products were fractionated by capillary electrophoresis.

The ability of the DNase I variant V7 S43K S206K to effectively digest DNA within the context of a DNA/RNA hybrid, while preserving the RNA, was assessed alongside a commercially available bovine DNase I (#M0303, NEB) and a variant of bovine DNase I, TURBO™ DNase (Thermo Fisher Scientific, Inc., Waltham, Massachusetts). A DNA/RNA duplex (60 basepairs) labeled with a different fluorophore on either strand (DNA=FAM=blue channel, RNA=ROX=red channel) was incubated with each DNase I in DNase I buffer (FIG. 7, substrate only panel and bovine DNase I panel), DNase I buffer plus 50 mM NaCl (FIG. 7, V7 S43K S206K panel) or TURBO™ DNase Buffer (FIG. 7, bottom panel). Reaction products were fractionated by capillary electrophoresis. While all the enzymes tested specifically digest the DNA strand (grey) of a DNA/RNA hybrid while leaving the RNA strand (black) intact, they do so with varying efficiencies. More DNA substrate remains after treatment with Bovine DNase I than either V7 S43K S206K DNase I or TURBO™ DNase. All DNases tested are less effective at degrading the DNA strand of a DNA/RNA hybrid under high $Mg^{2+}$ buffer conditions (not shown).

Example 9: Specificity of DNase I Variants for DNA over RNA

Figure 8:
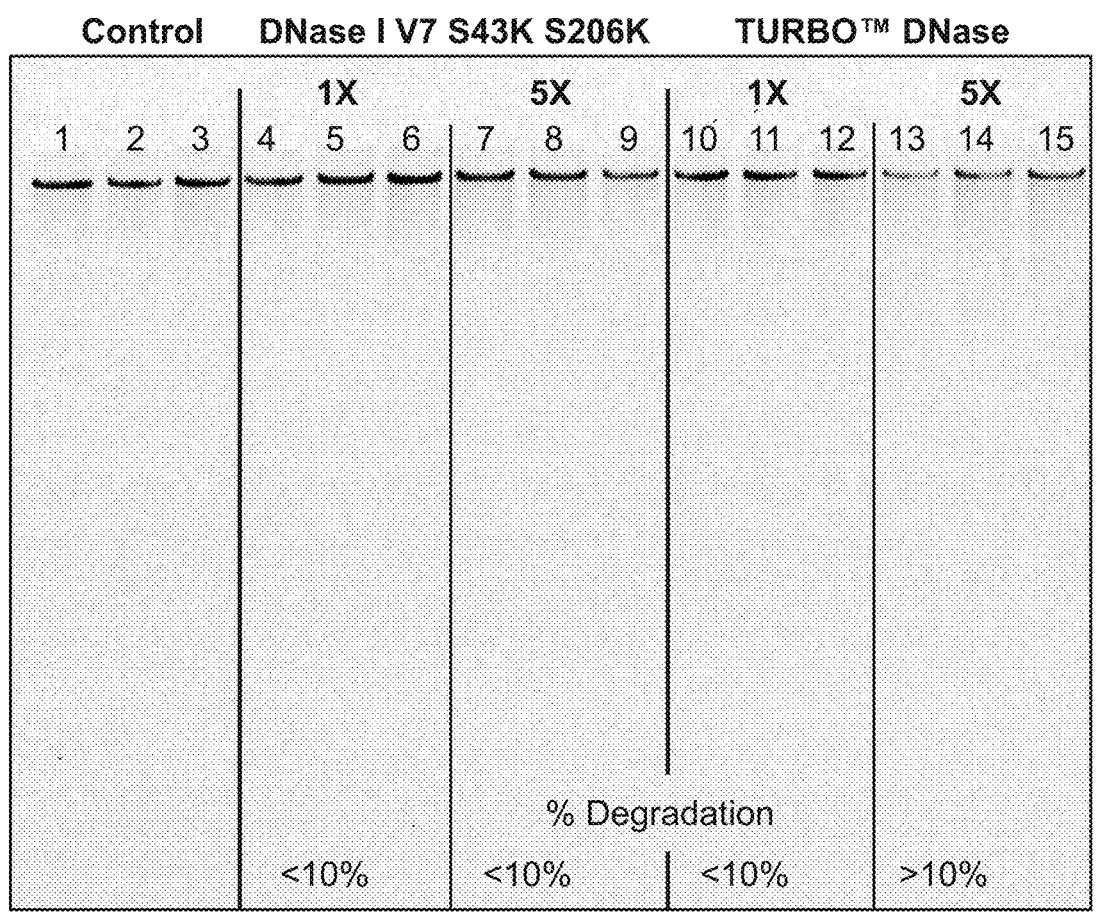
FIG. 8 shows the (in)ability of DNase V7 S43K S206K and TURBO™ DNase (at 1× and 5× concentrations) to digest RNA within a reaction was assessed by incubating similar amounts of enzyme (based on activity in TURBO™ DNase Reaction Buffer) in triplicate with a fluorescently labeled RNA (300 nts) for 16 h at 37° C. in 1× NEBuffer 4 (NEB #B7004). RNA was resolved by PAGE and the extent of RNA preservation or digestion determined using densitometry.

The ability of DNase V7 S43K S206K and TURBO™ DNase to leave intact RNA in a reaction was assessed by incubating similar amounts of enzyme (based on activity in TURBO™ DNase Reaction Buffer) in triplicate with a fluorescently labeled RNA (300 nts) for 16 h at 37° C. RNA was resolved by PAGE as shown in FIG. 8 and the extent of RNA preservation or digestion determined using densitometry. Both DNase I V7 S43K S206K and TURBO™ DNase preserve RNA when tested at 1× concentration, while some RNA digestion is observed with TURBO™ DNase at 5× concentration that is not observed with the V7 S43K S206K DNase I variant.

What is claimed is:

1. A DNase I variant having an amino acid sequence that is (a) at least 95% identical to SEQ ID NO:1 and (b) identical to SEQ ID NO:1 at one or more positions corresponding to L29, A35, D87, Q88, S94, P103, T108, P121, P132, A135, D145, E161, G172, P190, H208, and A224 of the polypeptide of SEQ ID NO:1, wherein said variant has DNase I activity.

2. The DNase I variant according to claim 1, wherein the amino acid sequence is identical to SEQ ID NO: 1 at one or more positions corresponding to E13, N18, S43, H44, N74, S75, P103, N106, T205, S206, and T207 of the polypeptide of SEQ ID NO: 1.

3. The DNase I variant according to claim 1, wherein the amino acid sequence comprises one or more substitutions at positions corresponding to SEQ ID NO:1, wherein the substitutions and corresponding positions are selected from A22S, R305, V46T, and V163I of the polypeptide of SEQ ID NO:1.

4. The DNase I variant according to claim 1, wherein the amino acid sequence comprises one or more substitutions at positions corresponding to SEQ ID NO:1, wherein the substitutions and corresponding positions are selected from E13K, E13R, N18A, A35V, S43K, S43R, H44K, H44R, N74K, N74R, S75K, S75R, P103S, N106A, T205K, T205R, S206K, S206R, T207K, and T207R of the polypeptide of SEQ ID NO:1.

5. The DNase I variant according to claim 1, wherein the amino acid sequence comprises two or more substitutions at positions corresponding to SEQ ID NO:1, wherein the substitutions and corresponding positions are selected from E13K, E13R, N18A, A35V, S43K, S43R, H44K, H44R, N74K, N74R, S75K, S75R, P103S, N106A, T205K, T205R, S206K, S206R, T207K, and T207R of the polypeptide of SEQ ID NO:1.

6. The DNase I variant according to claim 1, wherein the amino acid sequence comprises three or more substitutions at positions corresponding to SEQ ID NO:1, the substitutions and corresponding positions selected from E13K, E13R, N18A, A35V, S43K, S43R, H44K, H44R, N74K, N74R, S75K, S75R, P103S, N106A, T205K, T205R, S206K, S206R, T207K, and T207R of the polypeptide of SEQ ID NO: 1.

7. A DNase I variant having an amino acid sequence (I) that is at least 95% identical to SEQ ID NO:1 and (II) that comprises one or more of:
(a) a lysine or arginine at a position corresponding to position 13 of the polypeptide of SEQ ID NO:1,
(b) a lysine or arginine at a position corresponding to position 43 of the polypeptide of SEQ ID NO:1,
(c) a lysine or arginine at a position corresponding to position 44 of the polypeptide of SEQ ID NO:1,
(d) a lysine or arginine at a position corresponding to position 74 of the polypeptide of SEQ ID NO:1,
(e) a lysine or arginine at a position corresponding to position 75 of the polypeptide of SEQ ID NO:1,
(f) a lysine or arginine at a position corresponding to position 205 of the polypeptide of SEQ ID NO:1,
(g) a lysine or arginine at a position corresponding to position 206 of the polypeptide of SEQ ID NO:1,
(h) a lysine or arginine at a position corresponding to position 207 of the polypeptide of SEQ ID NO:1; and
wherein said variant has DNase I activity.

8. The DNase I variant according to claim 7, wherein the amino acid sequence comprises two or more of:
(a) a lysine or arginine at a position corresponding to position 13 of the polypeptide of SEQ ID NO:1,
(b) a lysine or arginine at a position corresponding to position 43 of the polypeptide of SEQ ID NO:1,
(c) a lysine or arginine at a position corresponding to position 44 of the polypeptide of SEQ ID NO:1,
(d) a lysine or arginine at a position corresponding to position 74 of the polypeptide of SEQ ID NO:1,
(e) a lysine or arginine at a position corresponding to position 75 of the polypeptide of SEQ ID NO:1,
(f) a lysine or arginine at a position corresponding to position 205 of the polypeptide of SEQ ID NO:1,
(g) a lysine or arginine at a position corresponding to position 206 of the polypeptide of SEQ ID NO:1, and
(h) a lysine or arginine at a position corresponding to position 207 of the polypeptide of SEQ ID NO:1.

9. The DNase I variant according to claim 7, wherein the amino acid sequence comprises one or more of:
(a) a valine at a position corresponding to position 35 of SEQ ID NO:1, and
(b) a serine at a position corresponding to position 103 of SEQ ID NO:1.

10. A DNase I variant having an amino acid sequence that is at least 98% identical to SEQ ID NO:1, wherein said variant has DNase I activity.

11. The DNase I variant according to claim 10, wherein the amino acid sequence is not identical to SEQ ID NO:1 at one or more positions corresponding to E13, N18, A35, S43, H44, N74, S75, P103, N106, T205, S206, and T207 of the polypeptide of SEQ ID NO:1.

12. A DNase I variant comprising an amino acid sequence identical to the amino acid sequence of SEQ ID NO: 1, 5, 7, 8, or 9.

13. The DNase I variant according claim 1, wherein the DNase I variant has at least 30% of its peak catalytic activity in the presence of a total salt concentration of 0 mM to 300 mM.

14. A DNase I variant having an amino acid sequence having at least 93% identity to SEQ ID NO:3 and comprising one or more substitutions at positions corresponding to SEQ ID NO:3, the substitutions and corresponding positions selected from N18A, S43K, S43R, S103X, N106A, S206K, S206R, T207K, and T207R, wherein said variant has DNase I activity.

15. A fusion protein comprising a single polypeptide chain, the single peptide chain comprising:
(a) the DNase I variant according to claim 1; and
(b) at least one of an affinity tag, a secretion signal, and a linker.

16. A method for hydrolyzing DNA comprising contacting (a) a composition comprising DNA and optionally RNA, and (b) the DNase I variant according to claim 1 to form a reaction mixture comprising DNA hydrolysis products.

17. The method according to claim 16, wherein the reaction mixture has a total salt concentration of 0 mM to 300 mM.

18. The method according to claim 16, wherein the composition comprises RNA and the reaction mixture comprises at least 90% of the RNA that was in the composition.

19. The method according to claim 16, wherein the reaction mixture comprises less than 10% of the DNA that was in the composition.

20. The method according to claim 16, wherein the reaction mixture further comprises a DNase I buffer or a high magnesium buffer.

21. A composition comprising the DNase I variant according to claim 1 and one or more salts at a total salt concentration of at least 50 mM.

22. The composition according to claim 21 further comprising one or more enzymes other than the DNase I variant.

23. A composition comprising the DNase I variant according to claim 1, wherein the composition has a form selected from a gel, a film, a powder, a cake, a dried form, and a lyophilized form.

24. A composition comprising the DNase I variant according to claim 1 and one or more of a monosaccharide, a disaccharide, a trisaccharide, a tetrasaccharide, starch, cellulose, dextrin, and dextran.

\* \* \* \* \*

UNITED STATES PATENT AND TRADEMARK OFFICE
CERTIFICATE OF CORRECTION

PATENT NO. : 11,993,792 B2
APPLICATION NO. : 17/332821
DATED : May 28, 2024
INVENTOR(S) : Heidi Crosby et al.

It is certified that error appears in the above-identified patent and that said Letters Patent is hereby corrected as shown below:

In the Claims

At Column 45, Line 21 Claim number 3, replace: "3. The DNase I variant according to Claim 1, wherein the amino acid sequence comprises one or more substitutions at positions corresponding to SEQ ID NO:1, wherein the substitutions and corresponding positions are selected from AS22, R305, V46T, and V163I of the polypeptide of SEQ ID NO:1." with: "3. The DNase I variant according to Claim 1, wherein the amino acid sequence comprises one or more substitutions at positions corresponding to SEQ ID NO:1, wherein the substitutions and corresponding positions are selected from A22S, R30S, V46T, and V163I of the polypeptide of SEQ ID NO:1."

Signed and Sealed this
Thirtieth Day of July, 2024

Katherine Kelly Vidal
*Director of the United States Patent and Trademark Office*

SEQUENCE LISTING

```
<160> NUMBER OF SEQ ID NOS: 12

<210> SEQ ID NO 1
<211> LENGTH: 260
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: DNase I variant V7 AA sequence

<400> SEQUENCE: 1

Leu Lys Ile Ala Ala Phe Asn Ile Arg Thr Phe Gly Glu Thr Lys Met
1               5                   10                  15

Ser Asn Ala Thr Leu Ala Ser Tyr Ile Val Arg Ile Leu Arg Arg Tyr
            20                  25                  30

Asp Ile Ala Leu Ile Gln Glu Val Arg Asp Ser His Leu Val Ala Val
        35                  40                  45

Gly Lys Leu Leu Asp Tyr Leu Asn Gln Asp Asp Pro Asn Thr Tyr His
    50                  55                  60
```

-continued

Tyr Val Val Ser Glu Pro Leu Gly Arg Asn Ser Tyr Lys Glu Arg Tyr
65                  70                  75                  80

Leu Phe Leu Phe Arg Pro Asp Gln Val Ser Val Leu Asp Ser Tyr Gln
            85                  90                  95

Tyr Asp Asp Gly Cys Glu Pro Cys Gly Asn Asp Thr Phe Ser Arg Glu
                100                 105                 110

Pro Ala Val Val Lys Phe Ser Ser Pro Ser Thr Lys Val Lys Glu Phe
                115                 120                 125

Ala Ile Val Pro Leu His Ala Ala Pro Ser Asp Ala Val Ala Glu Ile
            130                 135                 140

Asp Ser Leu Tyr Asp Val Tyr Leu Asp Val Gln Gln Lys Trp His Leu
145                 150                 155                 160

Glu Asp Val Met Leu Met Gly Asp Phe Asn Ala Gly Cys Ser Tyr Val
                165                 170                 175

Thr Ser Ser Gln Trp Ser Ser Ile Arg Leu Arg Thr Ser Pro Thr Phe
                180                 185                 190

Gln Trp Leu Ile Pro Asp Ser Ala Asp Thr Thr Ala Thr Ser Thr His
            195                 200                 205

Cys Ala Tyr Asp Arg Ile Val Val Ala Gly Ser Leu Leu Gln Ser Ala
210                 215                 220

Val Val Pro Gly Ser Ala Ala Pro Phe Asp Phe Gln Ala Ala Tyr Gly
225                 230                 235                 240

Leu Ser Asn Glu Met Ala Leu Ala Ile Ser Asp His Tyr Pro Val Glu
            245                 250                 255

Val Thr Leu Thr
            260

<210> SEQ ID NO 2
<211> LENGTH: 260
<212> TYPE: PRT
<213> ORGANISM: Homo sapiens
<220> FEATURE:
<221> NAME/KEY: MISC_FEATURE
<223> OTHER INFORMATION: Human DNase I

<400> SEQUENCE: 2

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
                20                  25                  30

Asp Ile Ala Leu Val Gln Glu Val Arg Asp Ser His Leu Thr Ala Val
            35                  40                  45

Gly Lys Leu Leu Asp Asn Leu Asn Gln Asp Ala Pro Asp Thr Tyr His
50                  55                  60

Tyr Val Val Ser Glu Pro Leu Gly Arg Asn Ser Tyr Lys Glu Arg Tyr
65                  70                  75                  80

Leu Phe Val Tyr Arg Pro Asp Gln Val Ser Ala Val Asp Ser Tyr Tyr
            85                  90                  95

Tyr Asp Asp Gly Cys Glu Pro Cys Gly Asn Asp Thr Phe Asn Arg Glu
                100                 105                 110

Pro Ala Ile Val Arg Phe Phe Ser Arg Phe Thr Glu Val Arg Glu Phe
            115                 120                 125

Ala Ile Val Pro Leu His Ala Ala Pro Gly Asp Ala Val Ala Glu Ile
            130                 135                 140

Asp Ala Leu Tyr Asp Val Tyr Leu Asp Val Gln Glu Lys Trp Gly Leu

| | | | | |
|---|---|---|---|---|
|  | 145 | 150 | 155 | 160 |

Glu Asp Val Met Leu Met Gly Asp Phe Asn Ala Gly Cys Ser Tyr Val
                    165                  170                175

Arg Pro Ser Gln Trp Ser Ser Ile Arg Leu Trp Thr Ser Pro Thr Phe
            180                185                  190

Gln Trp Leu Ile Pro Asp Ser Ala Asp Thr Thr Ala Thr Pro Thr His
        195                  200              205

Cys Ala Tyr Asp Arg Ile Val Val Ala Gly Met Leu Leu Arg Gly Ala
    210                  215              220

Val Val Pro Asp Ser Ala Leu Pro Phe Asn Phe Gln Ala Ala Tyr Gly
225              230                235              240

Leu Ser Asp Gln Leu Ala Gln Ala Ile Ser Asp His Tyr Pro Val Glu
            245              250              255

Val Met Leu Lys
        260

<210> SEQ ID NO 3
<211> LENGTH: 260
<212> TYPE: PRT
<213> ORGANISM: Bos taurus
<220> FEATURE:
<221> NAME/KEY: MISC_FEATURE
<223> OTHER INFORMATION: Bovine DNase I

<400> SEQUENCE: 3

Leu Lys Ile Ala Ala Phe Asn Ile Arg Thr Phe Gly Glu Thr Lys Met
1              5                  10              15

Ser Asn Ala Thr Leu Ala Ser Tyr Ile Val Arg Ile Val Arg Arg Tyr
            20                25                30

Asp Ile Val Leu Ile Gln Glu Val Arg Asp Ser His Leu Val Ala Val
        35                  40              45

Gly Lys Leu Leu Asp Tyr Leu Asn Gln Asp Asp Pro Asn Thr Tyr His
    50                  55              60

Tyr Val Val Ser Glu Pro Leu Gly Arg Asn Ser Tyr Lys Glu Arg Tyr
65              70                75              80

Leu Phe Leu Phe Arg Pro Asn Lys Val Ser Val Leu Asp Thr Tyr Gln
            85                90                95

Tyr Asp Asp Gly Cys Glu Ser Cys Gly Asn Asp Ser Phe Ser Arg Glu
               100              105              110

Pro Ala Val Val Lys Phe Ser Ser His Ser Thr Lys Val Lys Glu Phe
            115              120              125

Ala Ile Val Ala Leu His Ser Ala Pro Ser Asp Ala Val Ala Glu Ile
    130                  135              140

Asn Ser Leu Tyr Asp Val Tyr Leu Asp Val Gln Gln Lys Trp His Leu
145              150                155              160

Asn Asp Val Met Leu Met Gly Asp Phe Asn Ala Asp Cys Ser Tyr Val
              165              170              175

Thr Ser Ser Gln Trp Ser Ser Ile Arg Leu Arg Thr Ser Ser Thr Phe
            180              185              190

Gln Trp Leu Ile Pro Asp Ser Ala Asp Thr Thr Ala Thr Ser Thr Asn
        195                200              205

Cys Ala Tyr Asp Arg Ile Val Val Ala Gly Ser Leu Leu Gln Ser Ser
    210                  215              220

Val Val Pro Gly Ser Ala Ala Pro Phe Asp Phe Gln Ala Ala Tyr Gly
225              230                235              240

Leu Ser Asn Glu Met Ala Leu Ala Ile Ser Asp His Tyr Pro Val Glu
            245                 250                 255

Val Thr Leu Thr
        260

<210> SEQ ID NO 4
<211> LENGTH: 816
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Encodes His-tagged DNase I variant V7 AA
      sequence
<220> FEATURE:
<221> NAME/KEY: misc_feature
<222> LOCATION: (781)..(816)
<223> OTHER INFORMATION: C-terminal His tag

<400> SEQUENCE: 4
cttaaaatcg ccgcgtttaa tattcgcacc tttggggaga ccaaaatgag caacgccaca      60
cttgcttcct atatcgtccg tatcttgcgc cgctatgaca tcgctctgat ccaagaggtt     120
cgcgataaac acttagtggc agtgggtaag ttactggact acctgaacca ggatgaccct     180
aatacttacc attacgtagt gtctgaacct ctgggtcgca actcttacaa agaacgctac     240 ctgttttttgt tccgtccgga ccaagtatcc gtcctggatt cataccaata cgacgatggt     300
tgtgagccct gcgggaacga cacgtttagt cgtgaacctg cggtggtgaa atttcgagt     360 ccttcaacaa aagtcaaaga atttgcgatt gtccctcttc acgcagcccc atcagacgct     420
gttgcggaga ttgactcact ttacgatgtc taccttgatg tccaacagaa gtggcatttg     480
gaggacgtta tgcttatggg agattttaat gcaggatgct cgtatgttac ttcatcgcag     540
tggtcgtcta tccgccttcg cacctcccct actttccagt ggctgatccc cgacagtgcc     600
gacacgactc ccaccaaaac tcactgtgca tacgatcgca ttgttgttgc tgggagtctt     660
ttacaaagtg cggttgtccc aggcagcgcc gcaccgttcg acttccaagc tgcctatggt     720
ttaagcaacg aaatggcgtt ggctatctct gaccattatc cagtagaagt cacgctgact     780
aatagcgccg tcgaccatca ccatcaccat cactga                               816

<210> SEQ ID NO 5
<211> LENGTH: 271
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: His-tagged DNase I variant V7 AA sequence
<220> FEATURE:
<221> NAME/KEY: MISC_FEATURE
<222> LOCATION: (261)..(271)
<223> OTHER INFORMATION: C-terminal His tag

<400> SEQUENCE: 5

Leu Lys Ile Ala Ala Phe Asn Ile Arg Thr Phe Gly Glu Thr Lys Met
1               5                   10                  15

Ser Asn Ala Thr Leu Ala Ser Tyr Ile Val Arg Ile Leu Arg Arg Tyr
            20                  25                  30

Asp Ile Ala Leu Ile Gln Glu Val Arg Asp Lys His Leu Val Ala Val
        35                  40                  45

Gly Lys Leu Leu Asp Tyr Leu Asn Gln Asp Asp Pro Asn Thr Tyr His

```
                50                  55                  60
Tyr Val Val Ser Glu Pro Leu Gly Arg Asn Ser Tyr Lys Glu Arg Tyr
 65                  70                  75                  80

Leu Phe Leu Phe Arg Pro Asp Gln Val Ser Val Leu Asp Ser Tyr Gln
                 85                  90                  95

Tyr Asp Asp Gly Cys Glu Pro Cys Gly Asn Asp Thr Phe Ser Arg Glu
                100                 105                 110

Pro Ala Val Val Lys Phe Ser Ser Pro Ser Thr Lys Val Lys Glu Phe
                115                 120                 125

Ala Ile Val Pro Leu His Ala Ala Pro Ser Asp Ala Val Ala Glu Ile
                130                 135                 140

Asp Ser Leu Tyr Asp Val Tyr Leu Asp Val Gln Gln Lys Trp His Leu
145                 150                 155                 160

Glu Asp Val Met Leu Met Gly Asp Phe Asn Ala Gly Cys Ser Tyr Val
                165                 170                 175

Thr Ser Ser Gln Trp Ser Ser Ile Arg Leu Arg Thr Ser Pro Thr Phe
                180                 185                 190

Gln Trp Leu Ile Pro Asp Ser Ala Asp Thr Thr Ala Thr Lys Thr His
                195                 200                 205

Cys Ala Tyr Asp Arg Ile Val Val Ala Gly Ser Leu Leu Gln Ser Ala
                210                 215                 220

Val Val Pro Gly Ser Ala Ala Pro Phe Asp Phe Gln Ala Ala Tyr Gly
225                 230                 235                 240

Leu Ser Asn Glu Met Ala Leu Ala Ile Ser Asp His Tyr Pro Val Glu
                245                 250                 255

Val Thr Leu Thr Asn Ser Ala Val Asp His His His His His His
                260                 265                 270

<210> SEQ ID NO 6
<211> LENGTH: 260
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: DNase I variant V7 AA sequence
<220> FEATURE:
<221> NAME/KEY: MISC_FEATURE
<222> LOCATION: (13)..(13)
<223> OTHER INFORMATION: x is any amino acid
<220> FEATURE:
<221> NAME/KEY: MISC_FEATURE
<222> LOCATION: (18)..(18)
<223> OTHER INFORMATION: x is any amino acid
<220> FEATURE:
<221> NAME/KEY: MISC_FEATURE
<222> LOCATION: (29)..(29)
<223> OTHER INFORMATION: x is any amino acid other than valine
<220> FEATURE:
<221> NAME/KEY: MISC_FEATURE
<222> LOCATION: (35)..(35)
<223> OTHER INFORMATION: x is any amino acid
<220> FEATURE:
<221> NAME/KEY: MISC_FEATURE
<222> LOCATION: (43)..(43)
<223> OTHER INFORMATION: x is any amino acid
<220> FEATURE:
<221> NAME/KEY: MISC_FEATURE
<222> LOCATION: (44)..(44)
<223> OTHER INFORMATION: x is any amino acid
<220> FEATURE:
<221> NAME/KEY: MISC_FEATURE
<222> LOCATION: (74)..(74)
<223> OTHER INFORMATION: x is any amino acid
```

```
<220> FEATURE:
<221> NAME/KEY: MISC_FEATURE
<222> LOCATION: (75)..(75)
<223> OTHER INFORMATION: x is any amino acid
<220> FEATURE:
<221> NAME/KEY: MISC_FEATURE
<222> LOCATION: (87)..(87)
<223> OTHER INFORMATION: x is any amino acid other than asparagine
<220> FEATURE:
<221> NAME/KEY: MISC_FEATURE
<222> LOCATION: (88)..(88)
<223> OTHER INFORMATION: x is any amino acid other than lysine
<220> FEATURE:
<221> NAME/KEY: MISC_FEATURE
<222> LOCATION: (94)..(94)
<223> OTHER INFORMATION: x is any amino acid other than threonine
<220> FEATURE:
<221> NAME/KEY: MISC_FEATURE
<222> LOCATION: (103)..(103)
<223> OTHER INFORMATION: x is any amino acid
<220> FEATURE:
<221> NAME/KEY: MISC_FEATURE
<222> LOCATION: (106)..(106)
<223> OTHER INFORMATION: x is any amino acid
<220> FEATURE:
<221> NAME/KEY: MISC_FEATURE
<222> LOCATION: (108)..(108)
<223> OTHER INFORMATION: x is any amino acid other than serine
<220> FEATURE:
<221> NAME/KEY: MISC_FEATURE
<222> LOCATION: (121)..(121)
<223> OTHER INFORMATION: x is any amino acid other than histidine
<220> FEATURE:
<221> NAME/KEY: MISC_FEATURE
<222> LOCATION: (132)..(132)
<223> OTHER INFORMATION: x is any amino acid other than alanine
<220> FEATURE:
<221> NAME/KEY: MISC_FEATURE
<222> LOCATION: (135)..(135)
<223> OTHER INFORMATION: x is any amino acid
<220> FEATURE:
<221> NAME/KEY: MISC_FEATURE
<222> LOCATION: (145)..(145)
<223> OTHER INFORMATION: x is any amino acid other than asparagine
<220> FEATURE:
<221> NAME/KEY: MISC_FEATURE
<222> LOCATION: (161)..(161)
<223> OTHER INFORMATION: x is any amino acid other than asparagine
<220> FEATURE:
<221> NAME/KEY: MISC_FEATURE
<222> LOCATION: (172)..(172)
<223> OTHER INFORMATION: x is any amino acid other than aspartate
<220> FEATURE:
<221> NAME/KEY: MISC_FEATURE
<222> LOCATION: (190)..(190)
<223> OTHER INFORMATION: x is any amino acid other than serine
<220> FEATURE:
<221> NAME/KEY: MISC_FEATURE
<222> LOCATION: (205)..(205)
<223> OTHER INFORMATION: x is any amino acid
<220> FEATURE:
<221> NAME/KEY: MISC_FEATURE
<222> LOCATION: (206)..(206)
<223> OTHER INFORMATION: x is any amino acid
<220> FEATURE:
<221> NAME/KEY: MISC_FEATURE
<222> LOCATION: (207)..(207)
<223> OTHER INFORMATION: x is any amino acid
<220> FEATURE:
<221> NAME/KEY: MISC_FEATURE
<222> LOCATION: (208)..(208)
<223> OTHER INFORMATION: x is any amino acid other than asparagine
<220> FEATURE:
<221> NAME/KEY: MISC_FEATURE
<222> LOCATION: (224)..(224)
<223> OTHER INFORMATION: x is any amino acid other than serine

<400> SEQUENCE: 6
```

```
Leu Lys Ile Ala Ala Phe Asn Ile Arg Thr Phe Gly Xaa Thr Lys Met
1               5                   10                  15

Ser Xaa Ala Thr Leu Ala Ser Tyr Ile Val Arg Ile Xaa Arg Arg Tyr
            20                  25                  30

Asp Ile Xaa Leu Ile Gln Glu Val Arg Asp Xaa Xaa Leu Val Ala Val
            35                  40                  45

Gly Lys Leu Leu Asp Tyr Leu Asn Gln Asp Asp Pro Asn Thr Tyr His
    50                  55                  60

Tyr Val Val Ser Glu Pro Leu Gly Arg Xaa Xaa Tyr Lys Glu Arg Tyr
65                  70                  75                  80

Leu Phe Leu Phe Arg Pro Xaa Xaa Val Ser Val Leu Asp Xaa Tyr Gln
                85                  90                  95

Tyr Asp Asp Gly Cys Glu Xaa Cys Gly Xaa Asp Xaa Phe Ser Arg Glu
                100                 105                 110

Pro Ala Val Val Lys Phe Ser Ser Xaa Ser Thr Lys Val Lys Glu Phe
            115                 120                 125

Ala Ile Val Xaa Leu His Xaa Ala Pro Ser Asp Ala Val Ala Glu Ile
    130                 135                 140

Xaa Ser Leu Tyr Asp Val Tyr Leu Asp Val Gln Gln Lys Trp His Leu
145                 150                 155                 160

Xaa Asp Val Met Leu Met Gly Asp Phe Asn Ala Xaa Cys Ser Tyr Val
                165                 170                 175

Thr Ser Ser Gln Trp Ser Ser Ile Arg Leu Arg Thr Ser Xaa Thr Phe
            180                 185                 190

Gln Trp Leu Ile Pro Asp Ser Ala Asp Thr Thr Ala Xaa Xaa Xaa Xaa
            195                 200                 205

Cys Ala Tyr Asp Arg Ile Val Val Ala Gly Ser Leu Leu Gln Ser Xaa
    210                 215                 220

Val Val Pro Gly Ser Ala Ala Pro Phe Asp Phe Gln Ala Ala Tyr Gly
225                 230                 235                 240

Leu Ser Asn Glu Met Ala Leu Ala Ile Ser Asp His Tyr Pro Val Glu
                245                 250                 255

Val Thr Leu Thr
            260

<210> SEQ ID NO 7
<211> LENGTH: 363
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: DNase I variant V7 AA sequence with dual tag
<220> FEATURE:
<221> NAME/KEY: MISC_FEATURE
<222> LOCATION: (1)..(92)
<223> OTHER INFORMATION: N-terminal chitin binding protein tag plus
      linker
<220> FEATURE:
<221> NAME/KEY: MISC_FEATURE
<222> LOCATION: (353)..(363)
<223> OTHER INFORMATION: C-terminal His tag

<400> SEQUENCE: 7

Asp Ser Trp Ala Val Thr Arg Ala Lys Glu Leu Asn Glu Gln Phe Val
1               5                   10                  15

Lys Gly Glu Leu Asn Gly Lys Asp Ser Cys Ser Asp Gly Glu Ile Ser
            20                  25                  30
```

```
Cys Thr Ala Asp Gly Lys Ile Ala Ile Cys Asn Tyr Gly Ala Trp Val
             35                  40                  45

Tyr Thr Glu Cys Ala Ala Gly Thr Thr Cys Phe Ala Tyr Asp Ser Gly
 50                  55                  60

Asp Ser Val Tyr Thr Ser Cys Asn Phe Thr Tyr Leu Lys Pro Asp Val
 65                  70                  75                  80

Val Phe Gly Gly Gly Ser Gly Gly Gly Ser Leu Lys Ile Ala
                 85                  90                  95

Ala Phe Asn Ile Arg Thr Phe Gly Glu Thr Lys Met Ser Asn Ala Thr
                100                 105                 110

Leu Ala Ser Tyr Ile Val Arg Ile Leu Arg Arg Tyr Asp Ile Ala Leu
                115                 120                 125

Ile Gln Glu Val Arg Asp Lys His Leu Val Ala Val Gly Lys Leu Leu
130                 135                 140

Asp Tyr Leu Asn Gln Asp Asp Pro Asn Thr Tyr His Tyr Val Val Ser
145                 150                 155                 160

Glu Pro Leu Gly Arg Asn Ser Tyr Lys Glu Arg Tyr Leu Phe Leu Phe
                165                 170                 175

Arg Pro Asp Gln Val Ser Val Leu Asp Ser Tyr Gln Tyr Asp Asp Gly
                180                 185                 190

Cys Glu Pro Cys Gly Asn Asp Thr Phe Ser Arg Glu Pro Ala Val Val
                195                 200                 205

Lys Phe Ser Ser Pro Ser Thr Lys Val Lys Glu Phe Ala Ile Val Pro
                210                 215                 220

Leu His Ala Ala Pro Ser Asp Ala Val Ala Glu Ile Asp Ser Leu Tyr
225                 230                 235                 240

Asp Val Tyr Leu Asp Val Gln Gln Lys Trp His Leu Glu Asp Val Met
                245                 250                 255

Leu Met Gly Asp Phe Asn Ala Gly Cys Ser Tyr Val Thr Ser Ser Gln
                260                 265                 270

Trp Ser Ser Ile Arg Leu Arg Thr Ser Pro Thr Phe Gln Trp Leu Ile
                275                 280                 285

Pro Asp Ser Ala Asp Thr Thr Ala Thr Lys Thr His Cys Ala Tyr Asp
290                 295                 300

Arg Ile Val Val Ala Gly Ser Leu Leu Gln Ser Ala Val Val Pro Gly
305                 310                 315                 320

Ser Ala Ala Pro Phe Asp Phe Gln Ala Ala Tyr Gly Leu Ser Asn Glu
                325                 330                 335

Met Ala Leu Ala Ile Ser Asp His Tyr Pro Val Glu Val Thr Leu Thr
                340                 345                 350

Asn Ser Ala Val Asp His His His His His
                355                 360

<210> SEQ ID NO 8
<211> LENGTH: 360
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: DNase I variant V7 AA sequence with a dual tag
<220> FEATURE:
<221> NAME/KEY: MISC_FEATURE
<222> LOCATION: (1)..(89)
<223> OTHER INFORMATION: N-terminal alpha mating factor
<220> FEATURE:
<221> NAME/KEY: MISC_FEATURE
```

<222> LOCATION: (350)..(360)
<223> OTHER INFORMATION: C-terminal His tag

<400> SEQUENCE: 8

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Leu Lys Ile Ala Ala Phe Asn
                85                  90                  95

Ile Arg Thr Phe Gly Glu Thr Lys Met Ser Asn Ala Thr Leu Ala Ser
            100                 105                 110

Tyr Ile Val Arg Ile Leu Arg Arg Tyr Asp Ile Ala Leu Ile Gln Glu
        115                 120                 125

Val Arg Asp Ser His Leu Val Ala Val Gly Lys Leu Leu Asp Tyr Leu
    130                 135                 140

Asn Gln Asp Asp Pro Asn Thr Tyr His Tyr Val Val Ser Glu Pro Leu
145                 150                 155                 160

Gly Arg Asn Ser Tyr Lys Glu Arg Tyr Leu Phe Leu Phe Arg Pro Asp
                165                 170                 175

Gln Val Ser Val Leu Asp Ser Tyr Gln Tyr Asp Asp Gly Cys Glu Pro
            180                 185                 190

Cys Gly Asn Asp Thr Phe Ser Arg Glu Pro Ala Val Val Lys Phe Ser
        195                 200                 205

Ser Pro Ser Thr Lys Val Lys Glu Phe Ala Ile Val Pro Leu His Ala
    210                 215                 220

Ala Pro Ser Asp Ala Val Ala Glu Ile Asp Ser Leu Tyr Asp Val Tyr
225                 230                 235                 240

Leu Asp Val Gln Gln Lys Trp His Leu Glu Asp Val Met Leu Met Gly
                245                 250                 255

Asp Phe Asn Ala Gly Cys Ser Tyr Val Thr Ser Ser Gln Trp Ser Ser
            260                 265                 270

Ile Arg Leu Arg Thr Ser Pro Thr Phe Gln Trp Leu Ile Pro Asp Ser
        275                 280                 285

Ala Asp Thr Thr Ala Thr Ser Thr His Cys Ala Tyr Asp Arg Ile Val
    290                 295                 300

Val Ala Gly Ser Leu Leu Gln Ser Ala Val Val Pro Gly Ser Ala Ala
305                 310                 315                 320

Pro Phe Asp Phe Gln Ala Ala Tyr Gly Leu Ser Asn Glu Met Ala Leu
                325                 330                 335

Ala Ile Ser Asp His Tyr Pro Val Glu Val Thr Leu Thr Asn Ser Ala
            340                 345                 350

Val Asp His His His His His His
        355                 360
```

<210> SEQ ID NO 9
<211> LENGTH: 260
<212> TYPE: PRT
<213> ORGANISM: Artificial Sequence

```
<220> FEATURE:
<223> OTHER INFORMATION: Synthetic construct
<220> FEATURE:
<221> NAME/KEY: MISC_FEATURE
<223> OTHER INFORMATION: DNase I variant V7+ AA sequence

<400> SEQUENCE: 9

Leu Lys Ile Ala Ala Phe Asn Ile Arg Thr Phe Gly Glu Thr Lys Met
1               5                   10                  15

Ser Asn Ala Thr Leu Ser Ser Tyr Ile Val Arg Ile Leu Ser Arg Tyr
            20                  25                  30

Asp Ile Ala Leu Ile Gln Glu Val Arg Asp Ser His Leu Thr Ala Val
        35                  40                  45

Gly Lys Leu Leu Asp Tyr Leu Asn Gln Asp Asp Pro Asn Thr Tyr His
    50                  55                  60

Tyr Val Val Ser Glu Pro Leu Gly Arg Asn Ser Tyr Lys Glu Arg Tyr
65                  70                  75                  80

Leu Phe Leu Phe Arg Pro Asp Gln Val Ser Val Leu Asp Ser Tyr Gln
                85                  90                  95

Tyr Asp Asp Gly Cys Glu Pro Cys Gly Asn Asp Thr Phe Ser Arg Glu
            100                 105                 110

Pro Ala Val Val Lys Phe Ser Ser Pro Ser Thr Lys Val Lys Glu Phe
        115                 120                 125

Ala Ile Val Pro Leu His Ala Ala Pro Ser Asp Ala Val Ala Glu Ile
    130                 135                 140

Asp Ser Leu Tyr Asp Val Tyr Leu Asp Val Gln Gln Lys Trp His Leu
145                 150                 155                 160

Glu Asp Ile Met Leu Met Gly Asp Phe Asn Ala Gly Cys Ser Tyr Val
                165                 170                 175

Thr Ser Ser Gln Trp Ser Ser Ile Arg Leu Arg Thr Ser Pro Thr Phe
            180                 185                 190

Gln Trp Leu Ile Pro Asp Ser Ala Asp Thr Thr Ala Thr Ser Thr His
        195                 200                 205

Cys Ala Tyr Asp Arg Ile Val Val Ala Gly Ser Leu Leu Gln Ser Ala
    210                 215                 220

Val Val Pro Gly Ser Ala Ala Pro Phe Asp Phe Gln Ala Ala Tyr Gly
225                 230                 235                 240

Leu Ser Asn Glu Met Ala Leu Ala Ile Ser Asp His Tyr Pro Val Glu
                245                 250                 255

Val Thr Leu Thr
            260

<210> SEQ ID NO 10
<211> LENGTH: 260
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: DNase I variant V7+ AA sequence
<220> FEATURE:
<221> NAME/KEY: MISC_FEATURE
<222> LOCATION: (22)..(22)
<223> OTHER INFORMATION: x is any amino acid other than alanine
<220> FEATURE:
<221> NAME/KEY: MISC_FEATURE
<222> LOCATION: (29)..(29)
<223> OTHER INFORMATION: x is any amino acid other than valine
<220> FEATURE:
<221> NAME/KEY: MISC_FEATURE
```

```
<222> LOCATION: (30)..(30)
<223> OTHER INFORMATION: x is any amino acid other than arginine
<220> FEATURE:
<221> NAME/KEY: MISC_FEATURE
<222> LOCATION: (35)..(35)
<223> OTHER INFORMATION: x is any amino acid other than valine
<220> FEATURE:
<221> NAME/KEY: MISC_FEATURE
<222> LOCATION: (46)..(46)
<223> OTHER INFORMATION: x is any amino acid other than valine
<220> FEATURE:
<221> NAME/KEY: MISC_FEATURE
<222> LOCATION: (87)..(87)
<223> OTHER INFORMATION: x is any amino acid other than asparagine
<220> FEATURE:
<221> NAME/KEY: MISC_FEATURE
<222> LOCATION: (88)..(88)
<223> OTHER INFORMATION: x is any amino acid other than lysine
<220> FEATURE:
<221> NAME/KEY: MISC_FEATURE
<222> LOCATION: (94)..(94)
<223> OTHER INFORMATION: x is any amino acid other than threonine
<220> FEATURE:
<221> NAME/KEY: MISC_FEATURE
<222> LOCATION: (103)..(103)
<223> OTHER INFORMATION: x is any amino acid other than serine
<220> FEATURE:
<221> NAME/KEY: MISC_FEATURE
<222> LOCATION: (108)..(108)
<223> OTHER INFORMATION: x is any amino acid other than serine
<220> FEATURE:
<221> NAME/KEY: MISC_FEATURE
<222> LOCATION: (121)..(121)
<223> OTHER INFORMATION: x is any amino acid other than histidine
<220> FEATURE:
<221> NAME/KEY: MISC_FEATURE
<222> LOCATION: (132)..(132)
<223> OTHER INFORMATION: x is any amino acid other than alanine
<220> FEATURE:
<221> NAME/KEY: MISC_FEATURE
<222> LOCATION: (135)..(135)
<223> OTHER INFORMATION: x is any amino acid other than serine
<220> FEATURE:
<221> NAME/KEY: MISC_FEATURE
<222> LOCATION: (145)..(145)
<223> OTHER INFORMATION: x is any amino acid other than asparagine
<220> FEATURE:
<221> NAME/KEY: MISC_FEATURE
<222> LOCATION: (161)..(161)
<223> OTHER INFORMATION: x is any amino acid other than asparagine
<220> FEATURE:
<221> NAME/KEY: MISC_FEATURE
<222> LOCATION: (163)..(163)
<223> OTHER INFORMATION: x is any amino acid other than valine
<220> FEATURE:
<221> NAME/KEY: MISC_FEATURE
<222> LOCATION: (172)..(172)
<223> OTHER INFORMATION: x is any amino acid other than aspartate
<220> FEATURE:
<221> NAME/KEY: MISC_FEATURE
<222> LOCATION: (190)..(190)
<223> OTHER INFORMATION: x is any amino acid other than serine
<220> FEATURE:
<221> NAME/KEY: MISC_FEATURE
<222> LOCATION: (208)..(208)
<223> OTHER INFORMATION: x is any amino acid other than asparagine
<220> FEATURE:
<221> NAME/KEY: MISC_FEATURE
<222> LOCATION: (224)..(224)
<223> OTHER INFORMATION: x is any amino acid other than serine

<400> SEQUENCE: 10

Leu Lys Ile Ala Ala Phe Asn Ile Arg Thr Phe Gly Glu Thr Lys Met
 1               5                  10                  15

Ser Asn Ala Thr Leu Xaa Ser Tyr Ile Val Arg Ile Xaa Xaa Arg Tyr
            20                  25                  30
```

```
Asp Ile Xaa Leu Ile Gln Glu Val Arg Asp Ser His Leu Xaa Ala Val
            35                  40                  45

Gly Lys Leu Leu Asp Tyr Leu Asn Gln Asp Asp Pro Asn Thr Tyr His
 50                  55                  60

Tyr Val Val Ser Glu Pro Leu Gly Arg Asn Ser Tyr Lys Glu Arg Tyr
 65                  70                  75                  80

Leu Phe Leu Phe Arg Pro Xaa Xaa Val Ser Val Leu Asp Xaa Tyr Gln
                 85                  90                  95

Tyr Asp Asp Gly Cys Glu Xaa Cys Gly Asn Asp Xaa Phe Ser Arg Glu
            100                 105                 110

Pro Ala Val Val Lys Phe Ser Ser Xaa Ser Thr Lys Val Lys Glu Phe
            115                 120                 125

Ala Ile Val Xaa Leu His Xaa Ala Pro Ser Asp Ala Val Ala Glu Ile
            130                 135                 140

Xaa Ser Leu Tyr Asp Val Tyr Leu Asp Val Gln Gln Lys Trp His Leu
145                 150                 155                 160

Xaa Asp Xaa Met Leu Met Gly Asp Phe Asn Ala Xaa Cys Ser Tyr Val
                165                 170                 175

Thr Ser Ser Gln Trp Ser Ser Ile Arg Leu Arg Thr Ser Xaa Thr Phe
            180                 185                 190

Gln Trp Leu Ile Pro Asp Ser Ala Asp Thr Thr Ala Thr Ser Thr Xaa
            195                 200                 205

Cys Ala Tyr Asp Arg Ile Val Val Ala Gly Ser Leu Leu Gln Ser Xaa
            210                 215                 220

Val Val Pro Gly Ser Ala Ala Pro Phe Asp Phe Gln Ala Ala Tyr Gly
225                 230                 235                 240

Leu Ser Asn Glu Met Ala Leu Ala Ile Ser Asp His Tyr Pro Val Glu
                245                 250                 255

Val Thr Leu Thr
            260

<210> SEQ ID NO 11
<211> LENGTH: 260
<212> TYPE: PRT
<213> ORGANISM: Artificial Sequence
<220> FEATURE:
<223> OTHER INFORMATION: Synnthetic construct
<220> FEATURE:
<221> NAME/KEY: misc_feature
<223> OTHER INFORMATION: DNase I variant AA sequence
<220> FEATURE:
<221> NAME/KEY: misc_feature
<222> LOCATION: (13)..(13)
<223> OTHER INFORMATION: x is any amino acid
<220> FEATURE:
<221> NAME/KEY: misc_feature
<222> LOCATION: (18)..(18)
<223> OTHER INFORMATION: x is any amino acid
<220> FEATURE:
<221> NAME/KEY: misc_feature
<222> LOCATION: (22)..(22)
<223> OTHER INFORMATION: x is any amino acid other than alanine
<220> FEATURE:
<221> NAME/KEY: misc_feature
<222> LOCATION: (29)..(29)
<223> OTHER INFORMATION: x is any amino acid other than valine
<220> FEATURE:
<221> NAME/KEY: misc_feature
<222> LOCATION: (30)..(30)
<223> OTHER INFORMATION: x is any amino acid other than arginine
<220> FEATURE:
<221> NAME/KEY: misc_feature
<222> LOCATION: (35)..(35)
<223> OTHER INFORMATION: x is any amino acid other than valine
```

-continued

```
<220> FEATURE:
<221> NAME/KEY: misc_feature
<222> LOCATION: (43)..(43)
<223> OTHER INFORMATION: x is any amino acid
<220> FEATURE:
<221> NAME/KEY: misc_feature
<222> LOCATION: (44)..(44)
<223> OTHER INFORMATION: x is any amino acid
<220> FEATURE:
<221> NAME/KEY: misc_feature
<222> LOCATION: (46)..(46)
<223> OTHER INFORMATION: x is any amino acid other than valine
<220> FEATURE:
<221> NAME/KEY: misc_feature
<222> LOCATION: (74)..(74)
<223> OTHER INFORMATION: x is any amino acid
<220> FEATURE:
<221> NAME/KEY: misc_feature
<222> LOCATION: (75)..(75)
<223> OTHER INFORMATION: x is any amino acid
<220> FEATURE:
<221> NAME/KEY: misc_feature
<222> LOCATION: (87)..(87)
<223> OTHER INFORMATION: x is any amino acid other than asparagine
<220> FEATURE:
<221> NAME/KEY: misc_feature
<222> LOCATION: (88)..(88)
<223> OTHER INFORMATION: x is any amino acid other than lysine
<220> FEATURE:
<221> NAME/KEY: misc_feature
<222> LOCATION: (94)..(94)
<223> OTHER INFORMATION: x is any amino acid other than theronine
<220> FEATURE:
<221> NAME/KEY: misc_feature
<222> LOCATION: (103)..(103)
<223> OTHER INFORMATION: x is any amino acid
<220> FEATURE:
<221> NAME/KEY: misc_feature
<222> LOCATION: (106)..(106)
<223> OTHER INFORMATION: x is any amino acid
<220> FEATURE:
<221> NAME/KEY: misc_feature
<222> LOCATION: (108)..(108)
<223> OTHER INFORMATION: x is any amino acid other than serine
<220> FEATURE:
<221> NAME/KEY: misc_feature
<222> LOCATION: (121)..(121)
<223> OTHER INFORMATION: x is any amino acid other than histidine
<220> FEATURE:
<221> NAME/KEY: misc_feature
<222> LOCATION: (132)..(132)
<223> OTHER INFORMATION: x is any amino acid other than alanine
<220> FEATURE:
<221> NAME/KEY: misc_feature
<222> LOCATION: (135)..(135)
<223> OTHER INFORMATION: x is any amino acid other than serine
<220> FEATURE:
<221> NAME/KEY: misc_feature
<222> LOCATION: (145)..(145)
<223> OTHER INFORMATION: x is any amino acid other than asparagine
<220> FEATURE:
<221> NAME/KEY: misc_feature
<222> LOCATION: (161)..(161)
<223> OTHER INFORMATION: x is any amino acid other than asparagine
<220> FEATURE:
<221> NAME/KEY: misc_feature
<222> LOCATION: (163)..(163)
<223> OTHER INFORMATION: x is any amino acid other than valine
<220> FEATURE:
<221> NAME/KEY: misc_feature
<222> LOCATION: (172)..(172)
<223> OTHER INFORMATION: x is any amino acid other than aspartate
<220> FEATURE:
<221> NAME/KEY: misc_feature
<222> LOCATION: (190)..(190)
<223> OTHER INFORMATION: x is any amino acid other than serine
<220> FEATURE:
<221> NAME/KEY: misc_feature
<222> LOCATION: (205)..(205)
```

```
<223> OTHER INFORMATION: x is any amino acid
<220> FEATURE:
<221> NAME/KEY: misc_feature
<222> LOCATION: (206)..(206)
<223> OTHER INFORMATION: x is any amino acid
<220> FEATURE:
<221> NAME/KEY: misc_feature
<222> LOCATION: (207)..(207)
<223> OTHER INFORMATION: x is any amino acid
<220> FEATURE:
<221> NAME/KEY: misc_feature
<222> LOCATION: (208)..(208)
<223> OTHER INFORMATION: x is any amino acid other than asparagine
<220> FEATURE:
<221> NAME/KEY: misc_feature
<222> LOCATION: (224)..(224)
<223> OTHER INFORMATION: x is any amino acid other than serine

<400> SEQUENCE: 11

Leu Lys Ile Ala Ala Phe Asn Ile Arg Thr Phe Gly Xaa Thr Lys Met
1               5                   10                  15

Ser Xaa Ala Thr Leu Xaa Ser Tyr Ile Val Arg Ile Xaa Xaa Arg Tyr
            20                  25                  30

Asp Ile Xaa Leu Ile Gln Glu Val Arg Asp Xaa Xaa Leu Xaa Ala Val
        35                  40                  45

Gly Lys Leu Leu Asp Tyr Leu Asn Gln Asp Asp Pro Asn Thr Tyr His
50                  55                  60

Tyr Val Val Ser Glu Pro Leu Gly Arg Xaa Xaa Tyr Lys Glu Arg Tyr
65                  70                  75                  80

Leu Phe Leu Phe Arg Pro Xaa Xaa Val Ser Val Leu Asp Xaa Tyr Gln
                85                  90                  95

Tyr Asp Asp Gly Cys Glu Xaa Cys Gly Xaa Asp Xaa Phe Ser Arg Glu
            100                 105                 110

Pro Ala Val Val Lys Phe Ser Ser Xaa Ser Thr Lys Val Lys Glu Phe
        115                 120                 125

Ala Ile Val Xaa Leu His Xaa Ala Pro Ser Asp Ala Val Ala Glu Ile
    130                 135                 140

Xaa Ser Leu Tyr Asp Val Tyr Leu Asp Val Gln Gln Lys Trp His Leu
145                 150                 155                 160

Xaa Asp Xaa Met Leu Met Gly Asp Phe Asn Ala Xaa Cys Ser Tyr Val
                165                 170                 175

Thr Ser Ser Gln Trp Ser Ser Ile Arg Leu Arg Thr Ser Xaa Thr Phe
            180                 185                 190

Gln Trp Leu Ile Pro Asp Ser Ala Asp Thr Thr Ala Xaa Xaa Xaa Xaa
        195                 200                 205

Cys Ala Tyr Asp Arg Ile Val Val Ala Gly Ser Leu Leu Gln Ser Xaa
    210                 215                 220

Val Val Pro Gly Ser Ala Ala Pro Phe Asp Phe Gln Ala Ala Tyr Gly
225                 230                 235                 240

Leu Ser Asn Glu Met Ala Leu Ala Ile Ser Asp His Tyr Pro Val Glu
                245                 250                 255

Val Thr Leu Thr
            260

<210> SEQ ID NO 12
<211> LENGTH: 35
<212> TYPE: DNA
<213> ORGANISM: Artificial Sequence
<220> FEATURE:
<223> OTHER INFORMATION: Synthetic construct
```

```
<400> SEQUENCE: 12
tctaagccgt gtacattttt tgtacacggc ttaga                                35
```